United States Patent
Chen et al.

(10) Patent No.: US 8,535,662 B2
(45) Date of Patent: Sep. 17, 2013

(54) APYRASE THERAPY FOR BLEEDING CONDITIONS

(75) Inventors: Ridong Chen, Naperville, IL (US); Soon Seog Jeong, Naperville, IL (US)

(73) Assignee: Apt Therapeutics, Inc., St. Louis, MO (US)

( * ) Notice: Subject to any disclaimer, the term of this patent is extended or adjusted under 35 U.S.C. 154(b) by 0 days.

(21) Appl. No.: 13/522,310

(22) PCT Filed: Jan. 13, 2011

(86) PCT No.: PCT/US2011/021170
§ 371 (c)(1),
(2), (4) Date: Oct. 9, 2012

(87) PCT Pub. No.: WO2011/088231
PCT Pub. Date: Jul. 21, 2011

(65) Prior Publication Data
US 2013/0028880 A1    Jan. 31, 2013

Related U.S. Application Data

(60) Provisional application No. 61/294,725, filed on Jan. 13, 2010.

(51) Int. Cl.
*A61K 38/46* (2006.01)

(52) U.S. Cl.
USPC .......................................... 424/94.6; 435/195

(58) Field of Classification Search
None
See application file for complete search history.

(56) References Cited

U.S. PATENT DOCUMENTS

| | | |
|---|---|---|
| 7,247,300 B1 | 7/2007 | Chen et al. |
| 7,390,485 B2 | 6/2008 | Jeong et al. |
| 2009/0003539 A1 | 1/2009 | Baird et al. |

OTHER PUBLICATIONS

Bahit et al., "Current Trials in Acute Myocardial Infarction," Cardiol. Special Ed. (2001) 7(2):49-55.
Brodie, "What Anti-thrombotic Therapy is Best with Primary PCIi for Acute ST Elevation Myocardial Infarction: How Should the Horizons Trial Change Current Practice?" Catheterization and Cardiovascular Interventions (2008) 71:816-821.
Chorich et al., "Hemorrhagic Ocular Complications Associated with the Use of Systemic Thrombolytic Agents," Opthalmology (1998) 105:428-431.
International Preliminary Report on Patentability for International Application No. PCT/US2011/021170, mailed May 9, 2012, 5 pages.
International Search Report and Written Opinion of the International Searching Authority for International Application No. PCT/US2011/021170, mailed Mar. 25, 2011, 9 pages.
Qyreshi et al., "Intracerebral Hemorrhages Associated with Neurointerventional Procedures Using a Combination of Antithrombotic Agents Including Abciximab," Stroke (2002) 33:1916-1919.

*Primary Examiner* — Jon P Weber
*Assistant Examiner* — Satyendra Singh
(74) *Attorney, Agent, or Firm* — Morrison & Foerster LLP

(57) ABSTRACT

This invention provides new methods of treating subjects experiencing or at risk of bleeding due to vascular injury, especially to the microvasculature and/or platelet desensitization. Examples of injury usefully treated by apyrase agents are pathophysiological conditions, ischemia reperfusion injury, injury from pharmacologic agents such as anticoagulants, antiplatelet agents, antithrombotics, thrombolytics, and/or immunosuppressants, and injury resulting from transplantation. Apyrase agents are also useful to maintain organ function when said organs are transplanted into an allogeneic recipient.

12 Claims, 11 Drawing Sheets

SEQUENCE LISTING

<160> NUMBER OF SEQ ID NOS: 2

<210> SEQ ID NO 1
<211> LENGTH: 529
<212> TYPE: PRT
<213> ORGANISM: Homo sapiens
<220> FEATURE:
<221> NAME/KEY: misc_feature
<222> LOCATION: (1)...(529)
<223> OTHER INFORMATION: CD39L3

```
<400> SEQUENCE: 1

Met Val Thr Val Leu Thr Arg Gln Pro Cys Glu Gln Ala Gly Leu Lys
 1               5                  10                  15

Ala Leu Tyr Arg Thr Pro Thr Ile Ile Ala Leu Val Val Leu Leu Val
            20                  25                  30

Ser Ile Val Val Leu Val Ser Ile Thr Val Ile Gln Ile His Lys Gln
        35                  40                  45

Glu Val Leu Pro Pro Gly Leu Lys Tyr Gly Ile Val Leu Asp Ala Gly
    50                  55                  60

Ser Ser Arg Thr Thr Val Tyr Val Tyr Gln Trp Pro Ala Glu Lys Glu
65                  70                  75                  80

Asn Asn Thr Gly Val Val Ser Gln Thr Phe Lys Cys Ser Val Lys Gly
                85                  90                  95

Ser Gly Ile Ser Ser Tyr Gly Asn Asn Pro Gln Asp Val Pro Arg Ala
            100                 105                 110

Phe Glu Glu Cys Met Gln Lys Val Lys Gly Gln Val Pro Ser His Leu
        115                 120                 125

His Gly Ser Thr Pro Ile His Leu Gly Ala Thr Ala Gly Met Arg Leu
    130                 135                 140

Leu Arg Leu Gln Asn Glu Thr Ala Ala Asn Glu Val Leu Glu Ser Ile
145                 150                 155                 160

Gln Ser Tyr Phe Lys Ser Gln Pro Phe Asp Phe Arg Gly Ala Gln Ile
                165                 170                 175

Ile Ser Gly Gln Glu Glu Gly Val Tyr Gly Trp Ile Thr Ala Asn Tyr
            180                 185                 190

Leu Met Gly Asn Phe Leu Glu Lys Asn Leu Trp His Met Trp Val His
        195                 200                 205

Pro His Gly Val Glu Thr Thr Gly Ala Leu Asp Leu Gly Gly Ala Ser
    210                 215                 220

Thr Gln Ile Ser Phe Val Ala Gly Glu Lys Met Asp Leu Asn Thr Ser
225                 230                 235                 240

Asp Ile Met Gln Val Ser Leu Tyr Gly Tyr Val Tyr Thr Leu Tyr Thr
                245                 250                 255

His Ser Phe Gln Cys Tyr Gly Arg Asn Glu Ala Glu Lys Lys Phe Leu
            260                 265                 270

Ala Met Leu Leu Gln Asn Ser Pro Thr Lys Asn His Leu Thr Asn Pro
        275                 280                 285

Cys Tyr Pro Arg Asp Tyr Ser Ile Ser Phe Thr Met Gly His Val Phe
    290                 295                 300

Asp Ser Leu Cys Thr Val Asp Gln Arg Pro Glu Ser Tyr Asn Pro Asn
305                 310                 315                 320

Asp Val Ile Thr Phe Glu Gly Thr Gly Asp Pro Ser Leu Cys Lys Glu
                325                 330                 335

Lys Val Ala Ser Ile Phe Asp Phe Lys Ala Cys His Asp Gln Glu Thr
            340                 345                 350

Cys Ser Phe Asp Gly Val Tyr Gln Pro Lys Ile Lys Gly Pro Phe Val
        355                 360                 365

Ala Phe Ala Gly Phe Tyr Tyr Thr Ala Ser Ala Leu Asn Leu Ser Gly
    370                 375                 380

Ser Phe Ser Leu Asp Thr Phe Asn Ser Ser Thr Trp Asn Phe Cys Ser
385                 390                 395                 400

Gln Asn Trp Ser Gln Leu Pro Leu Leu Leu Pro Lys Phe Asp Glu Val
                405                 410                 415
```

Tyr Ala Arg Ser Tyr Cys Phe Ser Ala Asn Tyr Ile Tyr His Leu Phe
            420                 425                 430

Val Asn Gly Tyr Lys Phe Thr Glu Glu Thr Trp Pro Gln Ile His Phe
            435                 440                 445

Glu Lys Glu Val Gly Asn Ser Ser Ile Ala Trp Ser Leu Gly Tyr Met
450                 455                 460

Leu Ser Leu Thr Asn Gln Ile Pro Ala Glu Ser Pro Leu Ile Arg Leu
465                 470                 475                 480

Pro Ile Glu Pro Pro Val Phe Val Gly Thr Leu Ala Phe Phe Thr Ala
                485                 490                 495

Ala Ala Leu Leu Cys Leu Ala Phe Leu Ala Tyr Leu Cys Ser Ala Thr
            500                 505                 510

Arg Arg Lys Arg His Ser Glu His Ala Phe Asp His Ala Val Asp Ser
            515                 520                 525

Asp

<210> SEQ ID NO 2
<211> LENGTH: 438
<212> TYPE: PRT
<213> ORGANISM: Artificial Sequence
<220> FEATURE:
<223> OTHER INFORMATION: synthetically constructed apyrase
<220> FEATURE:
<221> NAME/KEY: misc_feature
<222> LOCATION: (1)...(438)
<223> OTHER INFORMATION: CD39L3 R67G T69R

<400> SEQUENCE: 2

Glu Val Leu Pro Pro Gly Leu Lys Tyr Gly Ile Val Leu Asp Ala Gly
1               5                   10                  15

Ser Ser Gly Thr Arg Val Tyr Val Tyr Gln Trp Pro Ala Glu Lys Glu
            20                  25                  30

Asn Asn Thr Gly Val Val Ser Gln Thr Phe Lys Cys Ser Val Lys Gly
            35                  40                  45

Ser Gly Ile Ser Ser Tyr Gly Asn Asn Pro Gln Asp Val Pro Arg Ala
50                  55                  60

Phe Glu Glu Cys Met Gln Lys Val Lys Gly Gln Val Pro Ser His Leu
65                  70                  75                  80

His Gly Ser Thr Pro Ile His Leu Gly Ala Thr Ala Gly Met Arg Leu
            85                  90                  95

Leu Arg Leu Gln Asn Glu Thr Ala Ala Asn Glu Val Leu Glu Ser Ile
            100                 105                 110

Gln Ser Tyr Phe Lys Ser Gln Pro Phe Asp Phe Arg Gly Ala Gln Ile
        115                 120                 125

Ile Ser Gly Gln Glu Glu Gly Val Tyr Gly Trp Ile Thr Ala Asn Tyr
130                 135                 140

Leu Met Gly Asn Phe Leu Glu Lys Asn Leu Trp His Met Trp Val His
145                 150                 155                 160

Pro His Gly Val Glu Thr Thr Gly Ala Leu Asp Leu Gly Gly Ala Ser
            165                 170                 175

Thr Gln Ile Ser Phe Val Ala Gly Glu Lys Met Asp Leu Asn Thr Ser
            180                 185                 190

Asp Ile Met Gln Val Ser Leu Tyr Gly Tyr Val Tyr Thr Leu Tyr Thr
        195                 200                 205

His Ser Phe Gln Cys Tyr Gly Arg Asn Glu Ala Glu Lys Lys Phe Leu
    210                 215                 220

```
Ala Met Leu Leu Gln Asn Ser Pro Thr Lys Asn His Leu Thr Asn Pro
225                 230                 235                 240

Cys Tyr Pro Arg Asp Tyr Ser Ile Ser Phe Thr Met Gly His Val Phe
            245                 250                 255

Asp Ser Leu Cys Thr Val Asp Gln Arg Pro Glu Ser Tyr Asn Pro Asn
            260                 265                 270

Asp Val Ile Thr Phe Glu Gly Thr Gly Asp Pro Ser Leu Cys Lys Glu
            275                 280                 285

Lys Val Ala Ser Ile Phe Asp Phe Lys Ala Cys His Asp Gln Glu Thr
            290                 295                 300

Cys Ser Phe Asp Gly Val Tyr Gln Pro Lys Ile Lys Gly Pro Phe Val
305                 310                 315                 320

Ala Phe Ala Gly Phe Tyr Tyr Thr Ala Ser Ala Leu Asn Leu Ser Gly
                325                 330                 335

Ser Phe Ser Leu Asp Thr Phe Asn Ser Ser Thr Trp Asn Phe Cys Ser
            340                 345                 350

Gln Asn Trp Ser Gln Leu Pro Leu Leu Pro Lys Phe Asp Glu Val
        355                 360                 365

Tyr Ala Arg Ser Tyr Cys Phe Ser Ala Asn Tyr Ile Tyr His Leu Phe
    370                 375                 380

Val Asn Gly Tyr Lys Phe Thr Glu Glu Thr Trp Pro Gln Ile His Phe
385                 390                 395                 400

Glu Lys Glu Val Gly Asn Ser Ser Ile Ala Trp Ser Leu Gly Tyr Met
            405                 410                 415

Leu Ser Leu Thr Asn Gln Ile Pro Ala Glu Ser Pro Leu Ile Arg Leu
            420                 425                 430

Pro Ile Glu Pro Pro Val
            435
```

APYRASE THERAPY FOR BLEEDING CONDITIONS

CROSS-REFERENCE TO RELATED APPLICATIONS

This application is the national phase of PCT application PCT/US2011/021170 having an international filing date of 13 Jan. 2011, which claims benefit of U.S. Application No. 61/294,725 filed 13 Jan. 2010. The contents of the above patent applications are incorporated by reference herein in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 532602000700Seqlist.txt | Sep. 6, 2012 | 8,596 bytes |

TECHNICAL FIELD

The present invention relates to agents and methods for treating subjects with bleeding episodes or the risk of bleeding episodes associated with physical, mechanical, or pharmacological injury.

BACKGROUND ART

Bleeding frequently is the result of injury to the vascular system. Such injury can be caused by pathophysiological conditions, physical, mechanical, and/or pharmacologic insult.

For example, tPA administration for myocardial infarct is known to cause bleeding. In fact, the administration of anti-coagulant, antiplatelet, antithrombotic, and thrombolytic agents to treat infarct are generally known to result in risk of hemorrhage. Fatal intracerebral hemorrhage can be associated with using a combination of antithrombotic agents, including abciximab, in patients undergoing neurointerventional procedures, as reported by Qyreshi, et al., *Stroke* (2002) 33:1916-1919. Hemorrhagic ocular and orbital complications are known to be associated with the use of systemic thrombolytic agents, as reported by Chorich, et al., *Ophthalmology* (1998) 105:428-431. Hemorrhagic stroke (intracerebral hemorrhage) is primarily associated with arterial hypertension and amyloid angiopathy. Other causes include vascular malformations, intracranial aneurysms, arterial and venous thrombosis, coagulopathy, neoplastic, vasculitis, drug abuse, and trauma.

Bleeding can result from mechanical injury such as percutaneous coronary intervention, clot removal, etc. Moreover, primary percutaneous coronary intervention (PCI) for acute ST elevation myocardial infarction (STEMI) is co-treated with aspirin, clopidogrel, heparin and platelet glycoprotein IIb/IIIa inhibitors. However, heparin and glycoprotein IIb/IIIa inhibitors are associated with a high incidence of bleeding (Brodie, B. R., *Catheterization and Cardiovascular Interventions* (2008) 71:816-821).

Organ transplantation is associated with bleeding of the microvascular bed; indeed, ischemia/reperfusion injury is a related condition that results in bleeding.

Current fibrinolytic regimens involving concurrent use of tPA, aspirin and heparin is still limited by inadequate coronary reperfusion in up to 40% of patients and early thrombotic reocclusion in 5-10% patients (Bahit, M. C., et al., *Cardiol. Special Ed.* (2001) 7:49-55). Hence, there is a great need for an optimal antiplatelet agent that acts quickly without increasing the risk of bleeding. In addition, ideal agents would preserve vascular integrity and function, prevent inflammation damage, and improve metabolic tolerance to ischemia and enhance preconditioning type responses (Bahit, supra).

Moreover, needed in the art is a method of reducing bleeding or the risk of bleeding associated with physical, mechanical, or pharmacological injury.

DISCLOSURE OF THE INVENTION

It has now been discovered that apyrase agents are useful for treating or preventing bleeding associated with injury, especially injury to the microvasculature. As used herein, "bleeding" has its ordinary meaning—the escape of blood from the circulatory system per se. Thus, bleeding results in the presence of blood in locations other than arteries, veins and capillaries.

It is understood that apyrases, especially those with enhanced ADPase activity are useful in treating occlusive vascular diseases by virtue of their ability to hydrolyze ADP which is considered an agonist of platelet aggregation. (U.S. Pat. No. 7,390,485) Thus, apyrases are generally considered to be antagonists of blood clotting so it is somewhat counter-intuitive that they are also capable of decreasing, inhibiting or ameliorating bleeding. Thus, as part of the invention, the clinician will need to identify patients who are at risk for bleeding. For example, while the anti-occlusive effects of apyrase agents are useful in treatment of stroke, in some circumstances, such as treatment with tPA, the ability of apyrase agents to inhibit bleeding is indicated, and in those situations, the method of the invention is employed. For example, while previously it would not have been considered to treat hemorrhagic strokes using an apyrase agent, in view of the teachings of the present invention, it is understood that treatment of this patient population will be beneficial.

It should be emphasized that the suitable patient populations identified for treatment with an apyrase agent according to the present invention are not those that would have been identified based on the known antithrombotic activity of apyrase agents. Thus, the methods of the invention are practiced on populations that would not be taught by the prior art to be treated using apyrase agents.

In one embodiment, apyrase agents belong to the class of CD39 apyrases, e.g., CD39L1-10 apyrase, or in particular CD39L3 apyrases. In one embodiment, these apyrase agents are soluble as a result of absence of transmembrane domains.

Apyrase agents are useful in treating bleeding associated with pharmacologic agents that target thromboregulators or tissue rejection. For example, the pre-, co-, and/or post administration of apyrase agents with anticoagulants, antiplatelet agents, antithrombotics, thrombolytics, and/or immunosuppressants reduces associated bleeding.

Similarly, apyrase agents are useful to reduce bleeding associated with mechanical injury such PCI, stents, clot removal (e.g., sonication), transplantation, surgery, etc. In another embodiment, the mechanical injury is ischemia-reperfusion injury and administration of apyrase agents according to the present invention reduces the associated bleeding.

Thus, in one aspect, the invention is directed to a method to decrease bleeding or the risk of bleeding in a subject which method comprises administering to a subject in need of said decrease an effective amount of an apyrase agent.

Apyrase agents have also been found useful to maintain function and reduce inflammation in transplantation, especially in lung transplantation.

Thus in another aspect, the invention is directed to a method to maintain lung function and reduce inflammation in allogeneic lung transplantation subjects.

MODES OF CARRYING OUT THE INVENTION

Figure 1:
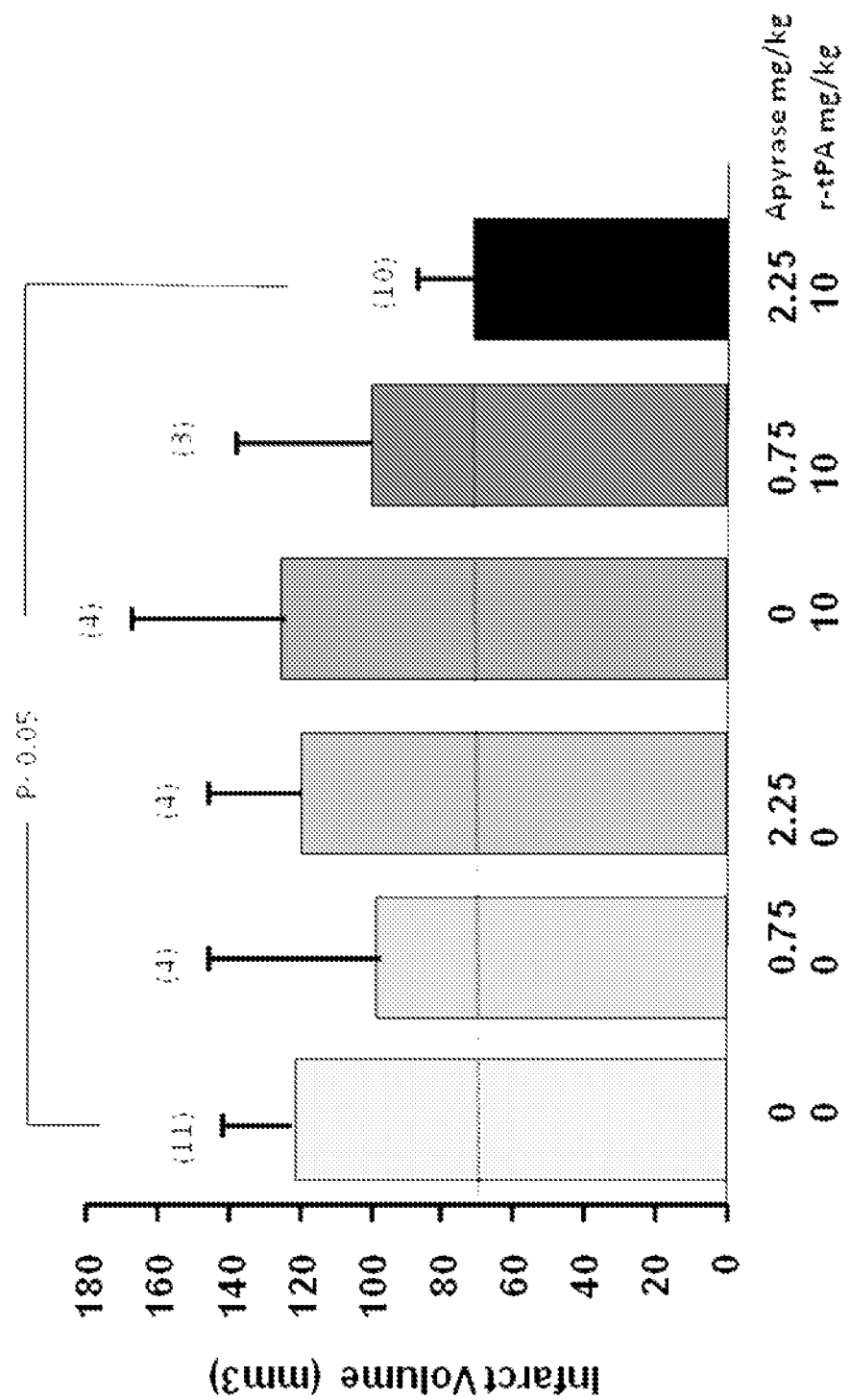
FIG. 1 shows infarct volume, in a rat stroke model comparing treatment with an apyrase agent plus tPA to treatment with either alone.

The present invention provides a use of apyrase agents that has hitherto been unappreciated. Specifically, apyrase administration is useful in decreasing the risk or the extent of bleeding in situations where bleeding occurs. The invention takes advantage of the understanding that there are certain conditions wherein bleeding is a problem and use of apyrases under these conditions is specifically indicated. In particular, the conditions include hemorrhagic stroke (as opposed to stroke in general), ischemic stroke where tPA or other agents that enhance bleeding are introduced to dissolve clots, surgical assaults where blood vessels are damaged, a problem particularly acute in surgical procedures in the elderly. Also indications are those where pharmacological agents which enhance bleeding are administered; the apyrase agents of the invention are administered to counteract over-response to these agents. As noted above, bleeding has its conventional meaning of the presence of blood outside of the circulatory system.

The treatment of hemorrhaging stroke is particularly important. Based on the anticoagulation activity or anti-thrombotic activity of apyrase agents, typically, prior to the disclosure of the present invention, apyrases would not be considered as treatments for this type of condition. However, in view of the contribution of the invention, while the use of an apyrase agent would have been contraindicated in this type of stroke, it is now understood that this type of stroke can in fact be treated with an apyrase agent.

"Transplantation" means attachment of an organ, tissue, limb, digit, or other body part (collectively, "biological material"). It is meant to include transplantation of material from a donor to a recipient and reattachment of the material where the donor is also the recipient. Optionally, transplantation involves surgical intervention and mechanical damage, e.g., surgical incisions.

"Treat" means a therapeutic or prophylactic action that either inhibits or reduces at least one clinically relevant index in an individual or in a population. "Treat", in the context of treating bleeding, includes a reduction in likelihood of local hemorrhage at the site of injury to the vasculature as well as in adjacent and distal tissue.

Compositions of the present invention are useful for treating bleeding that is associated with physical, mechanical, or pharmacological injury. Without being bound by theory, the applicants believe that mechanical or pharmacologic injury results in a cascade of events which lead to diminished structural integrity of the vasculature and the microvasculature, leading to bleeding. Surprisingly, it has been discovered that apyrase agents of the present invention reduce or prevent disruption of the microvasculature and are effective agents for treating bleeding.

Compositions of the present invention are also useful for preserving the function of transplanted organs. In particular, the apyrase agents are successful in maintaining lung function after allogeneic transplantation.

The subjects to be treated according to the methods of the invention include human subjects, veterinary subjects and mammalian subjects in general. They are useful in controlling variables in the conduct of research on laboratory models of various conditions. Thus, the subjects may be human, primate, canine, feline, rats, mice, rabbits and any other mammals.

Apyrase Agents

An apyrase agent can be any apyrase agent that has ATPase and ADPase activities. ATPase activity catalyzes the hydrolysis of phosphodiester bonds of adenosine triphosphate (ATP) to adenosine monophosphate (AMP) using two molecules of water. ADPase activity catalyzes the hydrolysis of adenosine diphosphate (ADP) to AMP using one molecule of water.

Certain apyrase agents can also hydrolyze other nucleoside triphosphates such as GTP, CTP, UTP, and other nucleoside diphosphates such as GDP, CDP, and UDP with various substrate specificities or preferences. The hydrolysis reactions catalyzed by apyrase agents require either calcium or magnesium as cofactor.

Apyrase agents can belong to one of several well-known families of apyrases. For example, an apyrase agent can belong to the CD39 class. By way of example, an apyrase agent can be a CD39L class agent (e.g., L1-L10). The CD39 apyrase agent can be soluble, e.g., sol CD39 or sol CD39L3. Genera and species of useful agents are described by Chen, et al. (U.S. Pat. No. 7,247,300) and by Jeong, et al. (U.S. Pat. No. 7,390,485). Additionally, apyrase agents include EN-apyrases taught in U.S. provisional patent application Ser. No. 61/294,695 co-filed on 13 Jan. 2010 entitled: "Therapeutic Apyrase Constructs, Agents, and Production Methods", hereby incorporated by reference in its entirety. Apyrase agents include apyrase homologs.

An apyrase agent can be a soluble calcium-activated nucleotidase (SCAN gi 20270339; SCAN-1 gi: 22218108; EC 3.6.1.6) as described by Smith, et al., *Arch. Biochem. Biophys.* (2002) 406:105-115. Such agents have sequence homology with the bed bug *Cimex lectularius* apyrase (gi: 4185746) Valenzuela, et al., *J. Biol. chem.* (1998) 273:30583-30590.

An apyrase agent can be a 5'-nucleotidase (gi: 33520072; EC 3.1.3.5), for example, as found in humans. Such agents have sequence homology with the mosquito *Aedes aegypti* apyrase (gi: 1703351) Champagne, et al., *Proc. Natl. Acad. Sci. USA* (1995) 92:694-698).

Useful apyrase agents can be an inositol polyphosphate 5'-phosphatase (gi: 346209; EC 3.1.3.56), for example, as occur in humans. Such agents have sequence homology with the *Rhodnius prolixus* apyrase (gi; 1546841) Sarkis, et al., *Biochem. J.,* (1986) 233:885-891.

An apyrase agent can be an agent modified to increase the ATPase or ADPase activities, thereby increasing the therapeutic activity according to the present invention. Examples of such agents (or "homologs") are sol CD39L3 R67G, sol CD39L3 R67G T69R (SEQ ID NO:3), and sol CD39L3 T69R, as taught in Chen, et al. (U.S. Pat. No. 7,247,300) and in Jeong, et al. (U.S. Pat. No. 7,390,485).

"Homologs", in reference to apyrase agents, are agents that have (1) structural similarity to a class of apyrase (e.g., as discussed above, CD39; SCAN, SCAN-1, 5'-nucleotidase, inositol polyphosphate 5'-phosphatase); (2) ADPase and ATPase activity; and (3) one or more substitutions (i.e., differences) from wild type apyrase. By "structurally similar" it is meant about or more than about any of 80% or 90% or 95% or 99% homology. Moreover, conservative substitutions, as they are now commonly known in the art, are expressly contemplated.

Without being bound by theory, an apyrase agent's bleeding-preventive efficacy is believed by the applicant to be based, in part, on the role of ADP and ATP in vascular endothelial cell (EC) damage; e.g., leading to increased vascular permeability and microvascular damage. ATP and ADP are released in high concentrations by activated EC and platelets following aggregation on endothelium. In turn, this activity further catalyzes additional platelet aggregation leading to microthrombus formation and the eventual worsening of endothelial injury. The activity of the instant apyrase agents block this ADP/ATP-mediated endothelial injury and bleeding.

An apyrase agent also helps to maintain homeostasis and prevent bleeding by re-sensitizing platelets. It has been known for several decades that platelets become desensitized and refractory to activation by collagen or ADP in vitro, or after major surgical operations possibly leading to an increased risk for postsurgical bleeding. Extracellular ADP binds to $P2Y_1$ receptors, leading to phosphorylation and then internalization of $P2Y_1$ receptors. This internalization of $P2Y_1$ receptors renders the platelet unresponsive (desensitized) to activation by collagen or additional extracellular ADP. Addition of apyrases in vitro protects the platelets from desensitization and restores platelet responsiveness. In vivo, apyrase-deficient mice had substantially prolonged bleeding times and purified mutant platelets failed to aggregate in response to standard platelet agonists in vitro (Enjyoji, K., et al., *Nat. Med.* (1999) 5:1011-1017). The internalization of $P2Y_1$ receptors compromises collagen-induced platelet activation and aggregation and leads to bleeding. This platelet hypofunction was reversed with administration of apyrases.

Unlike the irreversible $P2Y_{12}$ antagonists (e.g., clopidogrel or prasugrel), apyrases maintain the ability of platelets to bind collagen molecules; thereby providing a continuous level of homeostasis.

Treatment for Bleeding from Mechanical Injury

Ultrasound is found to increase thrombolysis in a variety of different conditions. Intravenous, Intraarterial, percutaneous or transcutaneous delivery of ultrasound alone or when used with thrombolytic agents like tPA, Urokinase, Alteplase, Streptokinase, PESDA (Perfluorocarbon Exposed Sonicated Dextrose Albumin) and RASDA (Room Air filled Sonicated Dextrose Albumin) increases clot lysis. Bleeding associated with ultrasound or ultrasound plus thrombolytic agents can be treated with apyrase agents.

Bleeding associated with mechanical injury from clot removal caused by microsnare can also be treated with apyrase agents. Similarly, transarterial suction thrombectomy can cause bleeding, treatable by apyrase agents. Bleeding from clot removal by aspiration through a balloon guide catheter or percutaneous transluminal cerebral balloon angioplasty can be treated by apyrase agents.

Percutaneous coronary interventions (PCI) (e.g., stent placement), cause trauma to the vessel wall and are associated with bleeding. Moreover, because mechanical injury can render the endoluminal surface thrombogenic, adjunctive antiplatelet agents are often administered. The instant apyrase agents reduce bleeding associated with mechanical injury or a combination of mechanical injury and pharmacologic injury (e.g., bleeding associated with antiplatelet, anticoagulants, antithrombotics, and/or thrombolytic agents).

It has been surprisingly discovered that apyrase agents of the present invention are useful in treating bleeding associated with ischemia-reperfusion injury (IRI). IRI is an injury that occurs after blood circulation is restarted in an organic tissue fallen into ischemia; e.g., accompanying excision or ablation procedures of various organs. Such injury also occurs when blood circulation is restarted after being stopped for the transplantation of an organ. IRI associated bleeding, treated by apyrase agents, can occur in any tissue, such as kidney, liver, lungs, pancreas, intestines, heart, and brain. IRI associated bleeding from transplantation can be treated by administering apyrase agents to the donor, the recipient, and/or to the stored organ.

Treatment for Bleeding Associated with Injury by Pharmacologic Agents

It has been discovered that apyrase agents of the present invention are useful for treating bleeding resulting from pharmacologic injury; e.g., caused by anticoagulants, antiplatelets, antithrombotics, and thrombolytics. Without being bound by theory, the applicants believe that the action of apyrase agents reduce endothelial cell activation and reduce neutrophil infiltration, local mediators of hemorrhage.

Bleeding from Thrombolytics

Fibrinolytic agents are used for treating blood clots, for example, ischemic stroke, thrombosis, pulmonary embolism, blocked catheters, and myocardial infarctions. Not surprisingly, these same agents that dissolve clots, cause an elevated risk of bleeding. Examples of thrombolytic compounds are streptokinase, urokinase, and tPA (e.g., alteplase), reteplase, tenecteplase, and anistreplase. Apyrase agents can be administered before, during, after, or simultaneously (e.g., as a dosage form) with a thrombolytic to reduce bleeding or the likelihood thereof.

Bleeding from Anticoagulants

Anticoagulants are often administered to stop thrombosis, for example, in deep vein thrombosis, pulmonary embolism, myocardial infarctions and strokes in those who are predisposed. Examples are Vitamin K antagonists (e.g., coumarines), heparins, and pentasaccharide inhibitors of factor Xa. Apyrase agents can be used to reduce the bleeding associated with anticoagulant therapy, apyrase agents can be administered before, during, after, or simultaneously (e.g., as a combination dosage form) with anticoagulant therapy.

Bleeding from Antiplatelet Agents

Antiplatelet agents are administered to prevent clot formation. They are widely used to prevent thrombolytic cerebrovascular disease. Examples of antiplatelet agents are the COX inhibitors (e.g., aspirin), phosphodiesterase inhibitors (cilostazol), glycoprotein IIb/IIIa inhibitors (e.g., ReoPro®, Integrilin®, Aggrastat®, and defibrotide), and adenosine reuptake inhibitors (e.g., dipyridamole), prostacyclin (e.g., epoprostenol). Apyrase agents can be used to reduce the bleeding associated with antiplatelet therapy. According to the present invention, apyrase agents can be administered before, during, after, or simultaneously (e.g., as a combination dosage form) with antiplatelet therapy.

Treatment of Risk of Bleeding from Underlying Medical Conditions

Stroke

Stroke, including both ischemic (under certain circumstances) and hemorrhagic stroke, is a medical condition associated with bleeding and is treatable with apyrase agents. Hemorrhagic stroke can be caused by pathophysiological conditions such as hypertension and amyloid angiopathy. Bleeding can result from ischemia reperfusion injury following removal of a blockage. Such blockage removal can be accomplished by pharmacologic treatment or mechanical disruption, either of which can cause bleeding. Bleeding also can result from spontaneous intracerebral hemorrhage. Accordingly, administration of apyrase agents during or after stroke can substantially reduce bleeding in subjects with such a condition.

Acute Myocardial Infarction Reperfusion

Patients who present with myocardial infarction (e.g., with ST segment elevation [STEMI]) are candidates for immediate reperfusion, either with thrombolytic therapy, percutaneous coronary intervention (PCI) or when these therapies are unsuccessful, bypass surgery. Each of these therapies are associated with bleeding and can usefully be treated or co-treated with apyrase agents. Moreover, following intervention, these patients are subject to bleeding associated with ischemia reperfusion injury, now treatable apyrase agents according to the present invention.

Tissue/Organ Transplant Therapy

Every year, more than 25,000 transplantation procedures are performed in the United States to replace solid organs, including the heart, intestine, kidney, liver, lung, and pancreas. Patients with conditions including end-stage renal disease, severe diabetes, advanced heart disease, and liver disease may undergo transplant procedures. One of the common side effects is excessive bleeding during or after surgery. Several factors can cause bleeding problems in organ transplant candidates, such as organ dysfunction or their medications. Frequently patients receive anticoagulants and have a decreased platelet count. Patients with end-stage liver disease may have excessive bleeding because the liver is no longer producing sufficient amounts of clotting factors. These conditions are now treatable according to the present invention by administration of apyrase agents.

Arteriovenous Fistulas

An arteriovenous fistula is an abnormal connection or passageway between an artery and a vein. It may be congenital, surgically created for hemodialysis treatments, or acquired due to pathologic process, such as trauma or erosion of an arterial aneurysm. Patients with an arteriovenous fistula frequently require an anti-thrombotic to prevent acute thrombosis but such treatment can lead to a risk of bleeding. Such bleeding can also be the further complication of surgery to vessels. For example, in a pig model of arteriovenous fistula, treatment with clopidogrel and heparin can result in bleeding at the surgical site. In the absence of clopidogrel and heparin treatment, thrombus formation results in the vessels during the surgery. Apyrase agent, according to the present invention, is a useful alone or as an adjunct therapy (e.g., with an antithrombotic) to reduce bleeding associated with arteriovenous fistula surgery.

Coronary Artery Bypass Surgery and Adjuvant Therapy

Bleeding associated with coronary artery bypass graft (CABG) surgery can result from ischemia reperfusion injury or from adjunct pharmacologic treatment such as administration of coagulation-fibrinolysis factors (fibrinogen, antithrombin-III, PAI-1 and tPA). Apyrase agents are useful for administering to CABG patients before, during, or after surgery. Apyrase agents are also useful for reducing the bleeding associated pharmacologic treatment when administered before, after, or simultaneously with (e.g., as a combination dosage form) with pharmacologic therapy.

Therapeutic Compositions and Administration of Apyrase Agents

The present invention provides compositions comprising a biologically effective amount of apyrase agent in a pharmaceutically acceptable dosage. Therapeutic compositions of apyrase agents may be administered to a patient before bleeding symptoms, during symptoms, or after symptoms.

Administration of apyrase agents to achieve therapeutic effect may be given by oral, transdermal, transmucosal, inhalation, or parenteral administration. Parenteral administration can be, e.g., by intravenous injection such as bolus injection, continuous infusion, sustained release, or other pharmaceutically acceptable techniques. Certain clinical situations may require administration of apyrase agents as a single effective dose, or may be administered daily for up to a week or a much as a month or more.

Ideally apyrase agents will be administered to patients in a pharmaceutically acceptable form containing physiologically acceptable carriers, excipients or diluents. Such diluents and excipients may be comprised of neutral buffered saline solution, antioxidants (for example ascorbic acid), low molecular weight polypeptides (for example polypeptides $\leq 10$ amino acids) amino acids, carbohydrates (for example, glucose, dextrose, sucrose, or dextrans), chelating agents such as EDTA, stabilizers (such as glutathione). Additionally, co-substrates for the apyrase agents, for example, calcium ($Ca^{2+}$) may be administered at time of dosage for maximal activity of the enzyme. Such carriers and diluents will be nontoxic to the patient at recommended dosages and concentrations.

When used to preserve organ function upon transplantation, the compositions containing apyrase agents may be applied to the organ prior to transplant or may be administered to the recipient of the transplant prior to, during the course of transplant or after transplant. Apyrase agents may be administered with other agents that enhance the benefit of apyrase agents alone. For example, administration of antiplatelets or anticoagulants, such as aspirin, heparin or bivalirudin with apyrase agents may have additional benefits such as improve reperfusion, extend therapeutic time window, prevent reocclusion, and prevent vascular thrombosis. Administration of apyrase agents may improve efficacy and lower the effective dosage of thrombolytics (tissue plasminogen activator (tPA), vampire bat plasminogen activator, urokinase, streptokinase, staphylokinase, and ancrod) or immunosuppressants. Operable fusion polypeptides between, for example, an ADP enhanced apyrase agent and thrombolytic (for example, tPA) may provide an ideal therapeutic solution for acute myocardial infarction (AMI), percutaneous coronary intervention (PCI) and acute ischemic stroke (AIS).

Dosage requirements of apyrase agents may vary significantly depending on age, race, weight, height, gender, duration of treatment, methods of administration, biological activity of apyrase agents, and severity of condition or other clinical variables. Effective dosages may be determined by a skilled physician or other skilled medical personnel.

The citations provided herein are hereby incorporated by reference for the cited subject matter.

The following examples are intended to illustrate but not to limit the invention. Moreover, scientific discussions below of underlying mechanisms gleaned from the data are also not meant as limitations.

EXAMPLES

The apyrase agent used in all of the following examples is a soluble apyrase agent derived from CD39L3 (SEQ ID NO:1).

```
                                            SEQ ID NO: 1
CD39L3
MVTVLTRQPCEQAGLKALYRTPTIIALVVLLVSIVVLVSITVIQIHKQEV

LPPGLKYGIVLDAGSSRTTVYVYQWPAEKENNTGVVSQTFKCSVKGSGIS

SYGNNPQDVPRAFEECMQKVKGQVPSHLHGSTPIHLGATAGMRLLRLQNE

TAANEVLESIQSYFKSQPFDFRGAQIISGQEEGVYGWITANYLMGNFLEK

NLWHMWVHPHGVETTGALDLGGASTQISFVAGEKMDLNTSDIMQVSLYGY

VYTLYTHSFQCYGRNEAEKKFLAMLLQNSPTKNHLTNPCYPRDYSISFTM

GHVFDSLCTVDQRPESYNPNDVITFEGTGDPSLCKEKVASIFDFKACHDQ

ETCSFDGVYQPKIKGPFVAFAGFYYTASALNLSGSFSLDTFNSSTWNFCS

QNWSQLPLLLPKFDEVYARSYCFSANYIYHLFVNGYKFTEETWPQIHFEK

EVGNSSIAWSLGYMLSLTNQIPAESPLIRLPIEPPVFVGTLAFFTAAALL

CLAFLAYLCSATRRKRHSEHAFDHAVDSD
```

The apyrase was prepared in CHO cells as described in U.S. provisional patent application Ser. No. 61/294,695, incorporated by reference. It is a glycosylated form of the amino acid sequence that spans positions 49-485 of SEQ ID NO:1 and is an R67G T69R mutant thereof designated sol CD39L3 R67G T69R. The amino acid sequence is shown as SEQ ID NO:2.

```
                                            SEQ ID NO: 2
sol CD39L3 R67G T69R
         3456789512345678961234567 8 971289
                                  8 9
EVLPPGLKYGIVLDAGSS G T R VYVYQWPAEKENNTGVVSQTFKCSVK

GSGISSYGNNPQDVPRAFEECMQKVKGQVPSHLHGSTPIHLGATAGMRLL

RLQNETAANEVLESIQSYFKSQPFDFRGAQIISGQEEGVYGWITANYLMG

NFLEKNLWHMWVHPHGVETTGALDLGGASTQISFVAGEKMDLNTSDIMQV

SLYGYVYTLYTHSFQCYGRNEAEKKFLAMLLQNSPTKNHLTNPCYPRDYS

ISFTMGHVFDSLCTVDQRPESYNPNDVITFEGTGDPSLCKEKVASIFDFK

ACHDQETCSFDGVYQPKIKGPFVAFAGFYYTASALNLSGSFSLDTFNSST

WNFCSQNWSQLPLLLPKFDEVYARSYCFSANYIYHLFVNGYKFTEETWPQ

IHFEKEVGNSSIAWSLGYMLSLTNQIPAESPLIRLPIEPPV
```

Example 1

Bleeding Associated with tPA in a Rat Stroke Model

This study used a clinically relevant embolic model in rats and shows that sol CD39L3 R67G T69R reduces the risk of intracranial hemorrhage associated with stroke, reduces the risk of intracranial hemorrhage associated with the administration of recombinant tissue plasminogen activator (r-tPA), and demonstrates the efficacy of apyrase agent to treat stroke (e.g., to reduce cerebral infarct volume and improve neurological deficit caused by the stroke).

The following groups were included in this study:
(1) control (saline treated), n=11;
(2) apyrase agent at 0.75 mg/kg, n=4;
(3) apyrase agent at 2.25 mg/kg, n=4;
(4) r-tPA (at 10 mg/kg), n=4;
(5) apyrase agent at 0.75 mg/kg plus r-tPA (10 mg/kg) and
(6) apyrase agent at 2.25 mg/kg plus r-tPA (10 mg/kg) (n=10).

Figure 2:
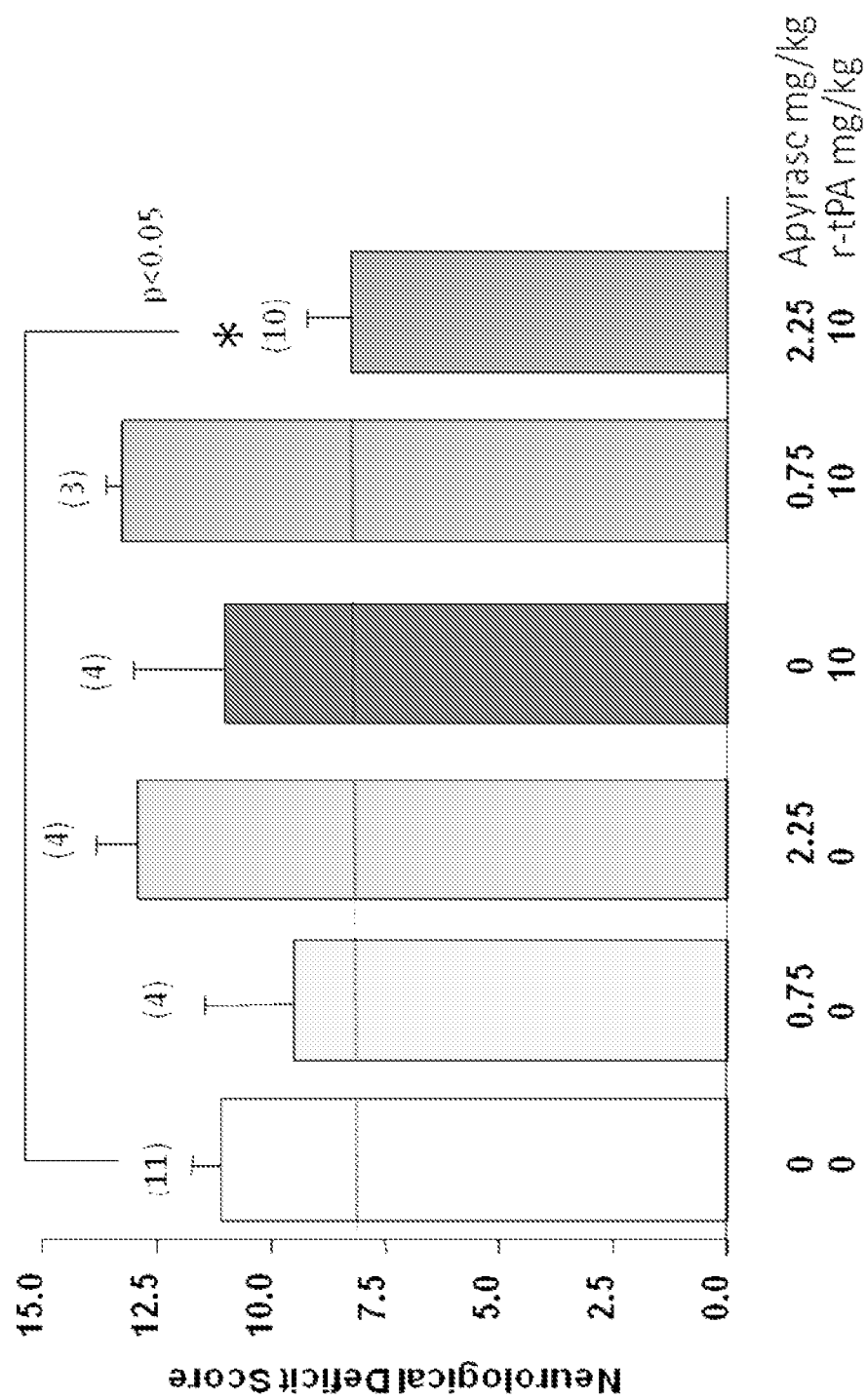
FIG. 2 shows neurologic deficit scores in the subjects shown in FIG. 1.

All the treatments were initiated at 2 h following thrombus injection into internal carotid artery. Infarct volume and behavioral deficit were determined at day 3 after the stroke. FIG. 1 shows that r-tPA at 10 mg/kg and apyrase agent at 2.25 mg/kg reduced infarct volume by 40% as compared to saline treated rats. FIG. 2 shows behavioral deficit, using footfault, forelimb placing and cylinder tests, that r-tPA at 10 mg/kg and apyrase agent at 2.25 mg/kg improved neurological deficit score by 30% as compared to saline treated rats.

Visual analysis of brains at 3 days after induction of ischemia demonstrated that 2-3 out of 11 rats with saline and 5 out of 11 animals treated with r-tPA alone demonstrated presence of petechial hemorrhages within the ischemia-affected aspects of the brain. In contrast, no hemorrhages in any of 10 rats treated with apyrase agent plus r-tPA was observed, as shown in Table 1.

TABLE 1

| Treatment | Hemorrhage #/total animals |
| --- | --- |
| Saline | 2/11 |
| Apyrase agent (0.75 mg/kg) | 0/4 |
| Apyrase agent (2.25 mg/kg) | 0/4 |
| r-tPA | 5/11 |
| r-tPA + Apyrase agent (0.75 mg/kg) | 0/3 |
| r-tPA + Apyrase agent (2.25 mg/kg) | 0/10 |

The results show that this apyrase agent reduces risk for tPA-induced hemorrhage.

Brain sections showing infarction and hemorrhage visually confirm there data.

Example 2

Use of Apyrase Agent Plus Aspirin to Provide Neuroprotection and Reduced Risk for Intracranial Hemorrhage in a Rat Model of Thromboembolic Stroke This example shows that sol CD39L3 R67G T69R alone or in combination with aspirin pretreatment reduces cerebral infarct volume, improves neurological deficit caused by stroke, and reduces the risk for intracranial hemorrhage.

In this study, four experimental groups were included (n=10):
(1) control, saline injected gastrically;
(2) aspirin, 1.25 mg/kg (equivalent to 100 mg/day dose in human) injected gastrically once a day, starting 3 days prior to middle cerebral artery (MCA) occlusion and also MCA occlusion until the end of each experiment;
(3) apyrase, dose at 0.75 mg/kg injected IV at 2 h after MCA occlusion;
(4) combination group, aspirin and apyrase agent.

In this clinically relevant embolic model, ischemic brain injury was induced by embolizing preformed clots into the middle cerebral artery (MCA). Ten microliters of blood were withdrawn into a catheter and retained for 15 min to allow formation of a clot. Once the clot was formed, the catheter was advanced 17 mm in the ICA until its tip was 1-2 mm away from the origin of the MCA. The preformed clot in the catheter was then injected, and the catheter was removed. Animal endpoints were measured 24 h after MCA occlusion.

Infarct Volume.

Infarct was measured in the brain section stained with 2,3,5-triphenyltetrazolium chloride (TTC) solution. The infarct volume was expressed as a percentage of the total volume from the ipsilateral hemisphere. In the control, the infarct volume was $30.01 \pm 2.97\%$ (mean±SD) at 24 h after MCA occlusion. Treatment of aspirin or apyrase agent alone reduced the infarct volume to $20.69 \pm 2.85\%$ and $17.89 \pm 2.35\%$, respectively, which was significantly smaller than the control group ($p<0.05$). Combination treatment of aspirin and apyrase agent reduced the infarct volume to $11.53 \pm 0.75\%$ which was significantly smaller than the aspirin alone groups. Compared to the control group, infarct volume of the combination group was significantly reduced by >60% ($p<0.05$).

Ischemic Brain Edema.

Brain swelling (edema) was determined using a formula: edema=(the volume of the right hemisphere—the volume of the left hemisphere)/the volume of the left hemisphere. Brain edema in the control group was $9.95 \pm 0.6\%$ at 24 h after the ischemic injury. Treatment of aspirin or apyrase agent alone reduced the edema to $6.81 \pm 0.56\%$ and $6.70 \pm 0.93\%$, respectively, which was significantly smaller than the control group ($p<0.05$). Combination treatment further reduced the edema to $4.16 \pm 0.42\%$ which was significantly smaller than the groups that received aspirin or apyrase agent alone. Compared to the control group, edema in the combination group was significantly reduced by 57% ($p<0.05$).

Neurological Deficits.

Neurological deficits were determined using a modified Bederson's scoring system as following: 0: no observable deficit; 1: forelimb flexion; 2: forelimb flexion plus decreased resistance to lateral push; 3: unidirectional circling; 4: unidirectional circling plus decreased level of consciousness.

Changes of neurological deficits at 4, 8, and 24 h in different groups are shown in Table 2.

TABLE 2

| Group | Neurological deficits. Median (interquartail rangez: $25^{th}$ to $75^{th}$) | | |
|---|---|---|---|
| (each n = 10) | 4 h | 8 h | 24 h |
| Control | 3.5 (2-4) | 2 (2-3.25) | 2 (2-3) |
| Aspirin (ASA) | 3 (2-4) | 2.5 (2-3) | 1.5 (1-2)* |

TABLE 2-continued

| Group | Neurological deficits. Median (interquartail rangez: $25^{th}$ to $75^{th}$) | | |
|---|---|---|---|
| (each n = 10) | 4 h | 8 h | 24 h |
| Apyrase agent | 3 (2-3) | 2 (2-3)* | 1.5 (1-2)* |
| ASA + Apyrase | 2 (2-3) | 2 (1.75-2)* | 1 (1-2)* |

*Significantly different from control group ($p < 0.5$)

At 4 h after MCA occlusion, all animals showed significant motor deficits, with median scores of 3.5 for control, 3 for both aspirin and apyrase agent alone groups, and 2 for the combination group. At 8 h after MCA occlusion neurological deficits were improved by apyrase agent alone and combination treatment. At 24 h after MCA occlusion, neurological deficits in the groups treated with aspirin, apyrase agent, or combination were all significantly less severe than the control group ($p<0.05$).

Hemorrhage.

Hemorrhagic transformation was quantified by detection of extracellular hemoglobin content in brain homogenates using Drabkin's reagents. Hemoglobin in the control group was $1.77 \pm 0.12$ at 24 h after the ischemic injury. Treatment of aspirin or apyrase agent alone reduced the hemoglobin to $0.93 \pm 0.11$ and $0.89 \pm 0.08$, respectively, which was significantly smaller than the control group ($p<0.05$). Compared to the control group, the hemoglobin in the aspirin plus apyrase agent combination group was reduced by 57%, being $0.78 \pm 0.12$ ($p<0.05$).

These results show that low-dose aspirin plus apyrase agent reduce infarct volume, improve neurological deficits and reduce risk for IR-related hemorrhage.

Example 3

Apyrase Agent Protection of Hyperglycemic Hemorrhage Transformation in a Rat Stroke Model This example shows sol CD39L3 R67G T69R reduces hyperglycemia-induced hemorrhagic transformation exaggeration in a rat focal ischemic model.

Focal ischemia was produced using the MCAO (Middle Cerebral Artery Occlusion) suture model in rats. Removal of the suture at 3.5 h after MCAO signaled the beginning of the reperfusion period. Ischemia-reperfusion causes blood extravasation into infracted brain tissues, showing multiple dots, small petechiae and more confluent petechial hemorrhage.

The animals were divided into three groups:
1) Control (n=6):
saline, IV at 3 h after MCAO over 30 min
2) Hyperglycemia (n=6)
25% glucose 2 g/kg, i.p. at 5 min after MCAO (Schurr, 2001) plus saline, IV at 3 h after MCAO over 30 min.
3) Hyperglycemia plus. sol CD39L3 R67G T69R (n=5)
25% glucose 2 g/kg, i.p. at 5 min after MCAO plus sol CD39L3 R67G T69R at 0.375 mg/kg in saline, IV at 3 h after MCAO over 30 min.

Rats were sacrificed at 8 h after MCAO and brains were frozen and cut into 20 μm frozen sections with intervals at 1 mm. The sections were stained with hematoxylin-eosin (HE) or cresyl violet. The H-E staining was used for measurements of hemorrhage rate and hemorrhage volume. The cresyl violet staining was used for quantifying infarct volume and brain swelling. An MCID™ digital image analysis system (Imaging Research, Inc, St. Catherines, Ontario, Canada) was used for quantifying hemorrhage and infarct volume.

In the group, hyperglycemia (Group 2) significantly increased hemorrhagic volume both in the cortex ($21.9 \pm 14.4$ mm$^3$ in the hyperglycemia group vs. $1.2 \pm 2.8$ mm$^3$ in the control group, (Group 1) $p<0.05$) and striatum ($11.1 \pm 5.3$ mm$^3$ in the hyperglycemia group vs. $1.7 \pm 1.0$ mm$^3$ in the control group, $p<0.01$). When sol CD39L3 R67G T69R (0.375 mg/kg) was infused intravenously 30 min before reperfusion (3 h after MCAO), hemorrhage volume was significantly decreased in the striatum ($4.8 \pm 2.0$ mm$^3$ in the sol CD39L3 R67G T69R group vs. $11.1 \pm 5.3$ mm$^3$ in the hyperglycemia group, $p<0.05$). Hyperglycemia also increased total infarct volume and brain edema in the cortex ($p<0.05$, compared with the control group) and worsened neurological function. sol CD39L3 R67G T69R (0.375 mg/kg) significantly improved neurological function at 4.5 hour after MCAO (data not shown).

Example 4

Apyrase Agent Treatment in Rabbits

Pharmacokinetic studies of apyrase agent (sol CD39L3 R67G T69R) were conducted in rabbits where a single bolus was injected intravenously. At various time points (10 min to 24 h after injection), rabbits were bled by cardiac puncture and serum was prepared. Serum samples were examined for both ADPase and ATPase activities. The half life of apyrase agent in the circulation was determined at approximately 24 h.

Time courses of the ex vivo effects of the recombinant apyrase agent and clopidogrel on ADP-induced platelet aggregation in platelet-rich plasma (PRP) were established after single bolus administration to rabbits (0.75 mg/kg for apyrase agent; 10 mg/kg for clopidogrel). Blood samples taken at various time points were heparinized.

Figure 3:
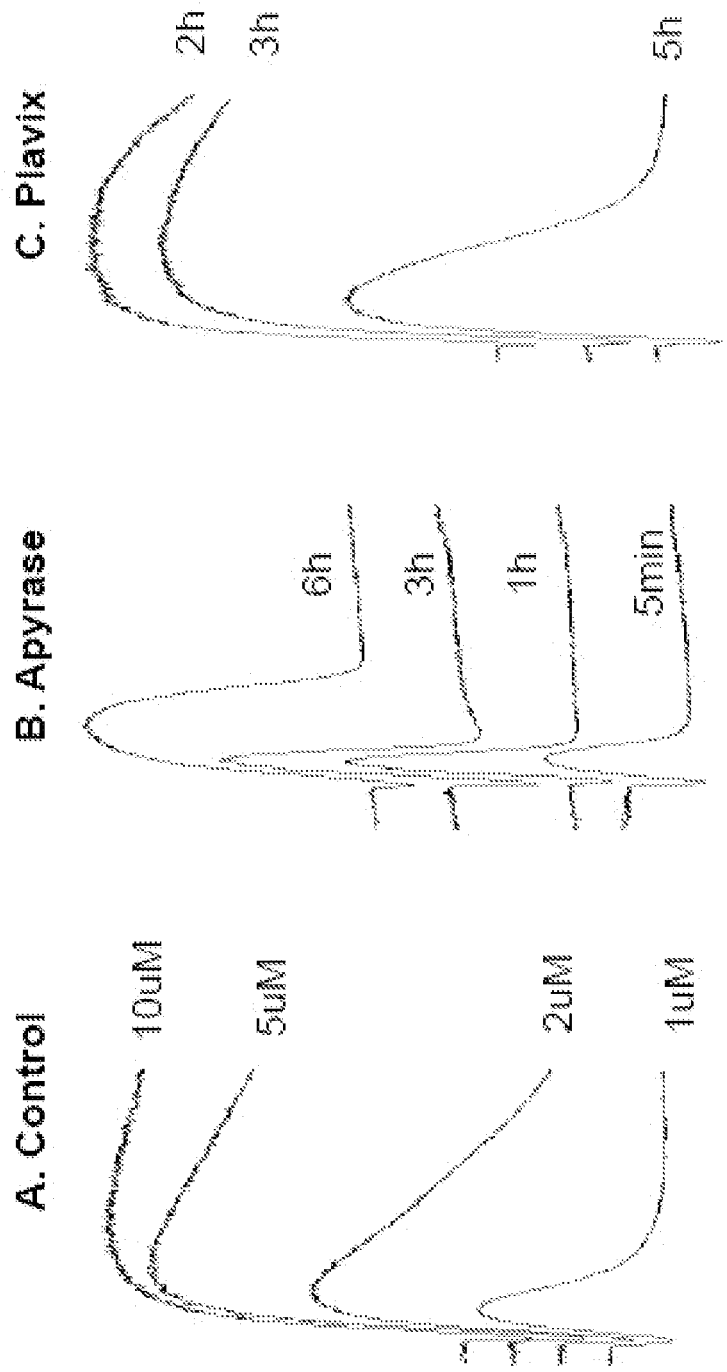
FIG. 3 shows inhibition of platelet aggregation as a function of time after IV injection of apyrase or Plavix® (clopidogrel).

FIG. 3 shows the inhibition of platelet aggregation as a function of time after IV injection of apyrase agent (0.75 mg/kg) or oral clopidogrel in rabbits (10 mg/kg). Panel A shows the dose-response of ADP-induced platelet aggregation for blood from rabbits administered vehicle. Panel B shows the inhibition of 10 mM ADP-induced platelet aggregation by apyrase agent. Panel C shows the inhibition of 10 mM ADP-induced platelet aggregation by clopidogrel (Plavix®). Data are presented as relative light transmission versus time.

The data demonstrate that apyrase agent at this dose is highly effective, achieving more than 95% inhibition of ADP-induced platelet aggregation. The strong effects observed at the first time point (5 min after dosing), suggest an early onset of antiplatelet action (FIG. 3B). Inhibition was long-lasting and still significant 6 h after dosing (70% inhibition). In contrast, clopidogrel exhibited much slower onset of action and significant effect was observed only 5 h after the treatment (FIG. 3C).

Bleeding risk was reduced with apyrase agent compared with clopidogrel and aspirin in rabbits. Rabbits were anesthetized with intramuscular ketamine/xylazine followed by inhaled isoflurane to maintain a stable level of surgical anesthesia for 5 h. Arterial blood pressure was monitored continuously and values for pressure and heart rate recorded at intervals after administration of apyrase agent and/or other antiplatelet agents. Venous blood samples were collected at baseline (before agents were given) for analysis of CBC and chemistry and samples were obtained serially for assay of prothrombin time (PT) and activated partial prothromboplastin time (aPTT). Template bleeding time was measured before and at intervals after administration of either a low or a high dose of apyrase agent (0.75 and 2.25 mg/kg, respectively), a clinically relevant dose of aspirin (10 mg/kg, Marlex Pharmaceuticals), clopidogrel (10 mg/kg, Bristol-Myers Squibb/Sanofi Pharmaceuticals Partnership), aspirin plus clopidogrel, or aspirin plus the low dose of apyrase agent (n=2-4/treatment). Apyrase agent was given as a single IV bolus and clopidogrel or aspirin were given by orogastric gavage (tablets were ground to a fine powder and administered as a slurry in 3-4 ml of 0.9% saline). Bleeding time was measured by making a 2 mm cut through the edge of the ear with a #11 surgical blade taking care to avoid visible veins as described previously. The cut portion of the ear was then immersed in 37° C. water and the time until bleeding stopped was noted. Bleeding time was measured at baseline, at time 0 (2 h after gavage of either aspirin, clopidogrel, or both) before IV administration of apyrase agent or saline vehicle, and 30 min, 3 and 24 h after IV administration of apyrase agent or saline vehicle.

All of the rabbits were healthy and exhibited values for CBC and chemistry within accepted normal ranges (data not shown). Platelet counts averaged $354 \pm 78$ thousand/cu. mm (n=25) and did not differ between treatment groups. Neither blood pressure nor heart rate changed significantly during the 3 h interval of monitoring after administration of apyrase agent and differences between treatment groups were negligible (data not shown). Bleeding time was not increased at any intervals compared with baseline after administration of either a low or high dose of apyrase agent. In contrast, gavage with aspirin caused increased bleeding time at 30 min (2.5 h after gavage), while gavage with clopidogrel increased bleeding time more markedly and at all intervals compared with baseline. The combination of apyrase agent and aspirin showed a significant increase in bleeding only at 30 min consistent with the increase observed with aspirin alone. Neither PT nor aPTT were changed significantly after administration of apyrase agent.

Example 5

Apyrase Agent for Treating Pigs Undergoing Percutaneous Coronary Intervention

Percutaneous coronary intervention (PCI) has become a cornerstone of care for patients with coronary artery disease with over 1 million patients each year receiving PCI for treatment of acute coronary syndromes or chronic angina. Because plaque rupture and vessel dissection are common problems associated with PCI, the use of stents that elute antiproliferative agents has been an important advance to decrease the rate of acute closure with thrombus and/or subsequent restenosis of the treated vessel. Nevertheless, acute thrombotic closure after PCI and stenting is still significant in the range of 6-11%, which has necessitated use of conjunctive anticoagulant as well as multiple antiplatelet agents and the search for better therapeutics because all of the current agents increase the risk of bleeding.

Time courses (5 min to 24 h) of ex vivo ADP-induced platelet aggregation in platelet-rich plasma were generated in pigs given either recombinant apyrase agent in combination with aspirin and heparin (as would occur during subsequent coronary catheterization studies), or clopidogrel plus aspirin and heparin, or aspirin and heparin alone as a control (n=2-3/treatment). sol CD39L3 R67G T69R was given as a single IV bolus (0.9-2.25 mg/kg) and clinically relevant doses of clopidogrel (8 mg/kg) and aspirin (10 mg/kg) were given by orogastric gavage (slurry in 20-30 ml of 0.9% saline).

All doses of apyrase agent achieved >95% inhibition of ADP-induced aggregation within 5 min after IV injection and platelet inhibition persisted for at least 5 h. In contrast, clopidogrel exhibited a much slower onset of action with significant inhibition of ADP-induced platelet aggregation beginning 5 h after dosing. By 24 h (the next time platelet aggregation was assessed in these studies), platelet aggregation had returned to normal in pigs given apyrase agent, whereas those given clopidogrel showed persistent inhibition of aggregation.

Example 6

Effects of Apyrase Agent on Early Thrombosis (24 h) and Neointimal Thickening and Luminal Stenosis (30 days) After Coronary Injury in Pigs Coronary injury with or without stenting in pigs is regarded as the best preclinical model for simulation of human angioplasty (Touchard, A. G., et al., *Thromb. Res.* (2007) 120:477-484). One coronary artery was injured by balloon overstretch in each pig and the site of injury including some overlap with the non-injured vessel was covered with a single bare metal stent (BMS).

Figure 4:
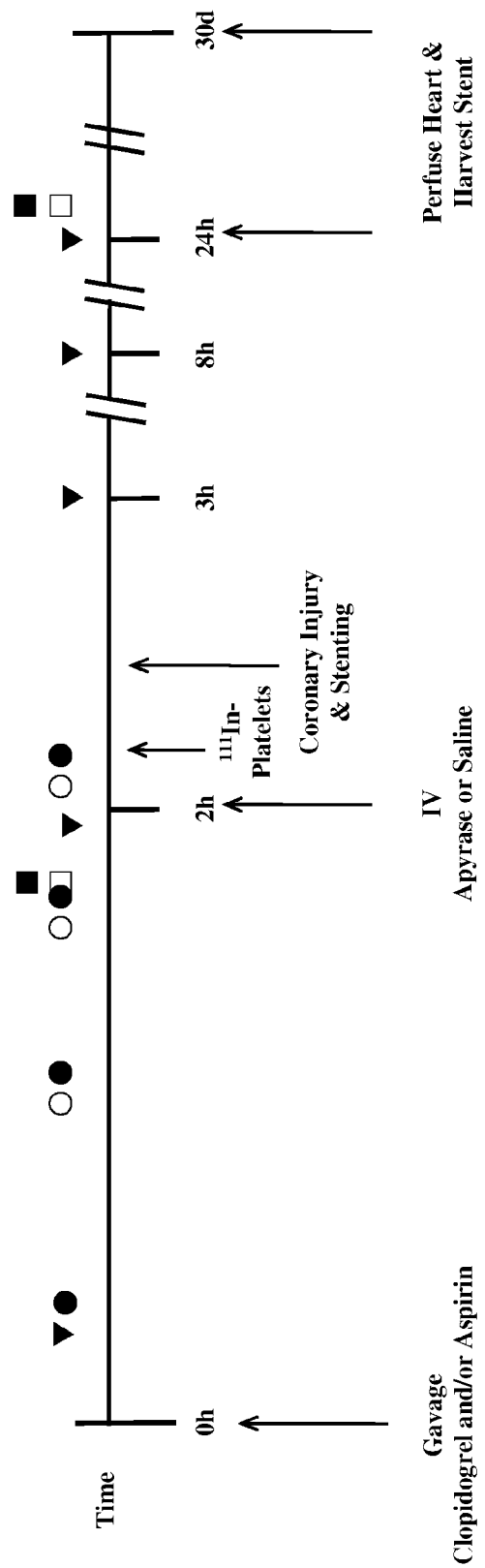
FIG. 4 shows timeline for a protocol to show safety and efficacy of apyrase agent in pigs.

Accumulation of $^{111}$In-labeled autologous platelets on the stents over the first 24 h was measured in 4/6 pigs in each group. Radiolabeled platelets were injected 15 min before the coronary catheterization and the hearts perfusion-fixed after 24 h to obtain the stented vessel segment for counting radiolabeled platelets. The timeline for the experiments is shown in FIG. 4. The treatment groups and doses of agents are summarized in Table 3.

TABLE 3

| Group | Drugs | Dosages | n |
|---|---|---|---|
| Apyrase | Apyase agent | 0.94 mg/kg | 6 |
|  | Aspirin | 10 mg/kg |  |
|  | Heparin | 150 U/kg* |  |

TABLE 3-continued

| Group | Drugs | Dosages | n |
|---|---|---|---|
| Clopidogrel** | Clopidogrel | 8 mg/kg | 6 |
|  | Aspirin | 10 mg/kg |  |
|  | Heparin | 150 U/kg* |  |
| Control | Aspirin | 10 mg/kg | 7 |
|  | Heparin | 150 U/kg* |  |

*150 U/kg initial dosage with additional full or half doses as required to keep Activated Clotting Time 3-4-fold above baseline.
**Clopidogrel was obtained from the pharmacy at Barnes-Jewish Hospital in St. Louis.

Accumulation of radiolabeled platelets on stented coronaries after 24 h was attenuated similarly by both apyrase agent and clopidogrel from $5.5 \times 10^5$ platelets/mm$^2$ to less than $4 \times 10^5$ platelets/mm$^2$. However, the difference compared with aspirin controls was not significant both because of the small 'n' and because of variability in the aspirin-treated pigs. Two of the pigs that received aspirin had low values for platelets on the vessel and stent comparable to the lowest values with apyrase agent or clopidogrel, while two others had values that were 4-5-fold higher. This resembles the phenomenon reported in patients given aspirin where some respond and show good inhibition of platelet function and others are resistant to the effect of aspirin. Microscopic analysis of arteries from two additional pigs in each treatment group 30 days after stenting revealed a qualitatively similar neointima in each treatment group, but one that occupied remarkably less volume for pigs given apyrase agent compared with other treatments. Pigs receiving apyrase agent showed an average luminal stenosis of 19.8±2% (calculated as the average of lumen area divided by area within the internal elastic lamina measured at proximal, middle and distal regions of the stent; for a total of six measurements in two pigs). However, pigs given aspirin alone or aspirin plus clopidogrel showed relatively higher levels of stenosis averaging 29.6±6% and 26.9±6%, respectively.

The hematology and blood chemistries in the pigs were within normal limits and did not differ between treatment groups (Table 4). More importantly, whole blood platelet counts were in the physiologic range and did not change appreciably over the first 24 h in any group (Table 5).

TABLE 4

| Apyrase | WBC (thns/uL) | RBC (mil/uL) | HGB (g/dL) | PCV (%) | Platelets (thns/uL) | Na (mmol/L) | K (mmol/L) |
|---|---|---|---|---|---|---|---|
|  | 17.9 | 4.6 | 8.6 | 28 | 484 | 140 | 4.9 |
|  | 13.0 | 4.9 | 7.8 | 23 | 381 | 130 | 4.1 |
|  | 12.7 | 4.8 | 8 | 23 | 267 | 140 | 4.4 |
|  | 9.7 | 5.0 | 8 | 23 | 171 | 140 | 4.3 |
|  | 10.4 | 3.7 | 6.4 | 19 | 199 | 142 | 3.9 |
|  | 10.5 | 4.5 | 8.5 | 25 | 369 | 137 | 3.4 |
| mean ± std. dev. | 12.4 ± 3.0 | 4.6 ± 0.5 | 7.9 ± 0.8 | 23 ± 3 | 312 ± 120 | 138 ± 4 | 4.2 ± 0.50 |
| Clopidogrel | 10.8 | 4.3 | 7.6 | 21.4 | 248 | 131 | 4.3 |
|  | 16.1 | 4.7 | 7.8 | 22.9 | 347 | 132 | 4.2 |
|  | 11.3 | 4.6 | 6.7 | 20.8 | 345 | 119 | 3.5 |
|  | 16.9 | 5.8 | 9.2 | 28 | 294 | 140 | 4.4 |
|  | 16.9 | 5.5 | 9 | 25 | 298 | 134 | 4.4 |
|  | 12 | 4.7 | 8.5 | 25.8 | 225 | 138 | 4.2 |
| mean ± std. dev. | 14.0 ± 2.9 | 4.9 ± 0.6 | 8.1 ± 1.0 | 24.0 ± 2.8 | 293 ± 50 | 132 ± 7 | 4.2 ± 0.3 |
| Aspirin | 10.3 | 5.19 | 9.3 | 26.8 | 301 | 135 | 3.5 |
|  | 16.4 | 4.75 | 8.1 | 27.7 | 498 | 140 | 3.3 |
|  | 13.2 | 4.9 | 8.1 | 23.9 | 355 | 138 | 3.6 |
|  | 13.9 | 5.07 | 8.1 | 22.8 | 499 | 144 | 3.2 |
|  | 13.3 | 4.52 | 7.2 | 20.7 | 213 | 117 | 2.7 |
| mean ± std. | 13.4 ± 2.2 | 4.89 ± 0.3 | 8.16 ± 0.8 | 24.4 ± 2.9 | 373 ± 125 | 135 ± 10.5 | 3.3 ± 0.4 |

TABLE 4-continued

| Apyrase | Cl (mmol/dL) | Glu (mg/dL) | BUN (mg/dL) | Creat (mg/dL) | AST (u/L) | ALT (u/L) | AlkPh (u/L) | Tot. Prot (g/dL) |
|---|---|---|---|---|---|---|---|---|
| | 101 | 20 | 10 | 0.9 | 47 | 40 | 126 | 4.7 |
| | 92 | 40 | 12 | 0.9 | 47 | 48 | 143 | 4.6 |
| | 100 | 78 | 8 | 0.9 | 25 | 20 | 119 | 4.0 |
| | 97 | 41 | 5 | 0.8 | 81 | 85 | 225 | 4.2 |
| | 103 | 91 | 3 | 0.9 | 165 | 80 | 64 | 3.8 |
| | 97 | 29 | 14 | 1.2 | 53 | 78 | 97 | 4.2 |
| mean ± std. dev. | 98 ± 4 | 50 ± 28 | 9 ± 4 | 0.9 ± 0.1 | 70 ± 50 | 59 ± 26 | 129 ± 54 | 4.3 ± 0.3 |
| Clopidogrel | 91 | 20 | 13 | 0.9 | 61 | 47 | 131 | 4.8 |
| | 92 | 33 | 12 | 0.9 | 63 | 65 | 111 | 5.2 |
| | 89 | 69 | 8 | 0.9 | 57 | 45 | 225 | 4.2 |
| | 98 | 40 | 7 | 1 | 31 | 45 | 180 | 4.5 |
| | 97 | 40 | 11 | 1 | 44 | 43 | 180 | 4.7 |
| | 99 | 30 | 5 | 0.9 | 64 | 77 | 184 | 4.6 |
| mean ± std. dev. | 94 ± 4 | 40 ± 17 | 9 ± 3 | 0.9 ± 0.1 | 53 ± 13 | 54 ± 14 | 169 ± 41 | 4.7 ± 0.3 |
| Aspirin | 93 | 30 | 12 | 1.1 | 45 | 48 | 95 | 6 |
| | 97 | 38 | 10 | 1.1 | 24 | 25 | 68 | 4.5 |
| | 97 | 49 | 4 | 1.1 | 38 | 52 | 132 | 4 |
| | 99 | 20 | 7 | 1.1 | 29 | 50 | 117 | 5 |
| | 88 | 58 | 11 | 0.9 | 211 | 106 | 235 | 4.2 |
| mean ± std. dev. | 95 ± 4.4 | 39 ± 15 | 9 ± 3.3 | 1.1 ± 0.1 | 69 ± 80 | 56 ± 30 | 129 ± 64 | 4.7 ± 0.8 |

TABLE 5

| | Baseline* | 24 hours |
|---|---|---|
| Apyrase (n = 6) | 311,833 + 120,224 | 345,750 + 67,935 |
| Clopidogrel (n = 6) | 292,833 + 49,588 | 296,688 + 121,810 |
| Aspirin (n = 5) | 373,200 + 125,108 | 475,750 + 75,447 |

*mean + std. dev. (thousands platelets)

Activated Clotting Time (ACT) was used to establish the adequacy of anticoagulation with heparin (150 U/kg) before coronary catheterization. Values increased from 119±15 sec (n=17) at baseline to 1114±286 sec after heparin (>9-fold baseline); greater than the 3-4-fold baseline threshold used commonly in clinical practice, but deemed necessary in pigs because of the tendency for hypercoagulability during vascular procedures. The elevated ACT level was maintained for one hour after coronary stenting by administration of additional doses of heparin as needed and did not differ between treatment groups.

Figure 5:
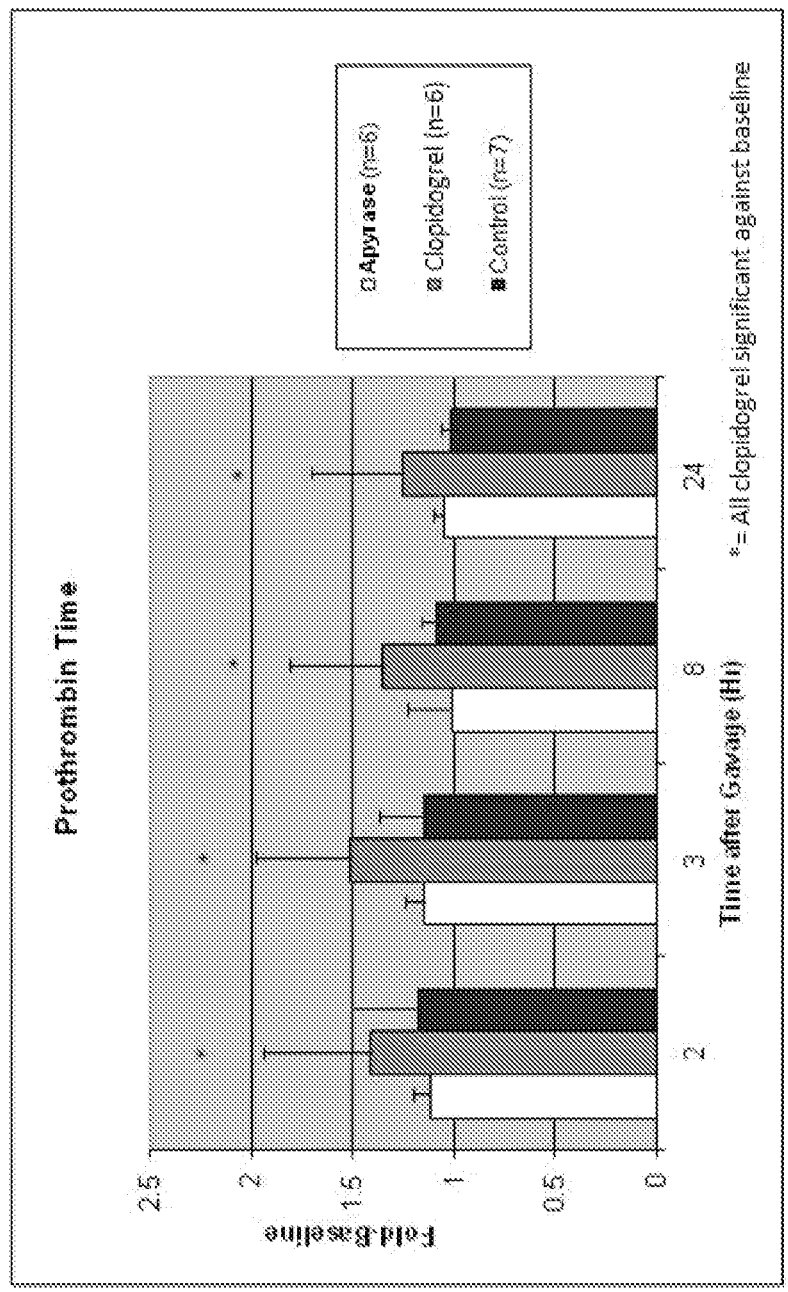
FIG. 5 shows prothrombin times (PT) for various time points after lavage in pigs subject to coronary injury.
Figure 6:
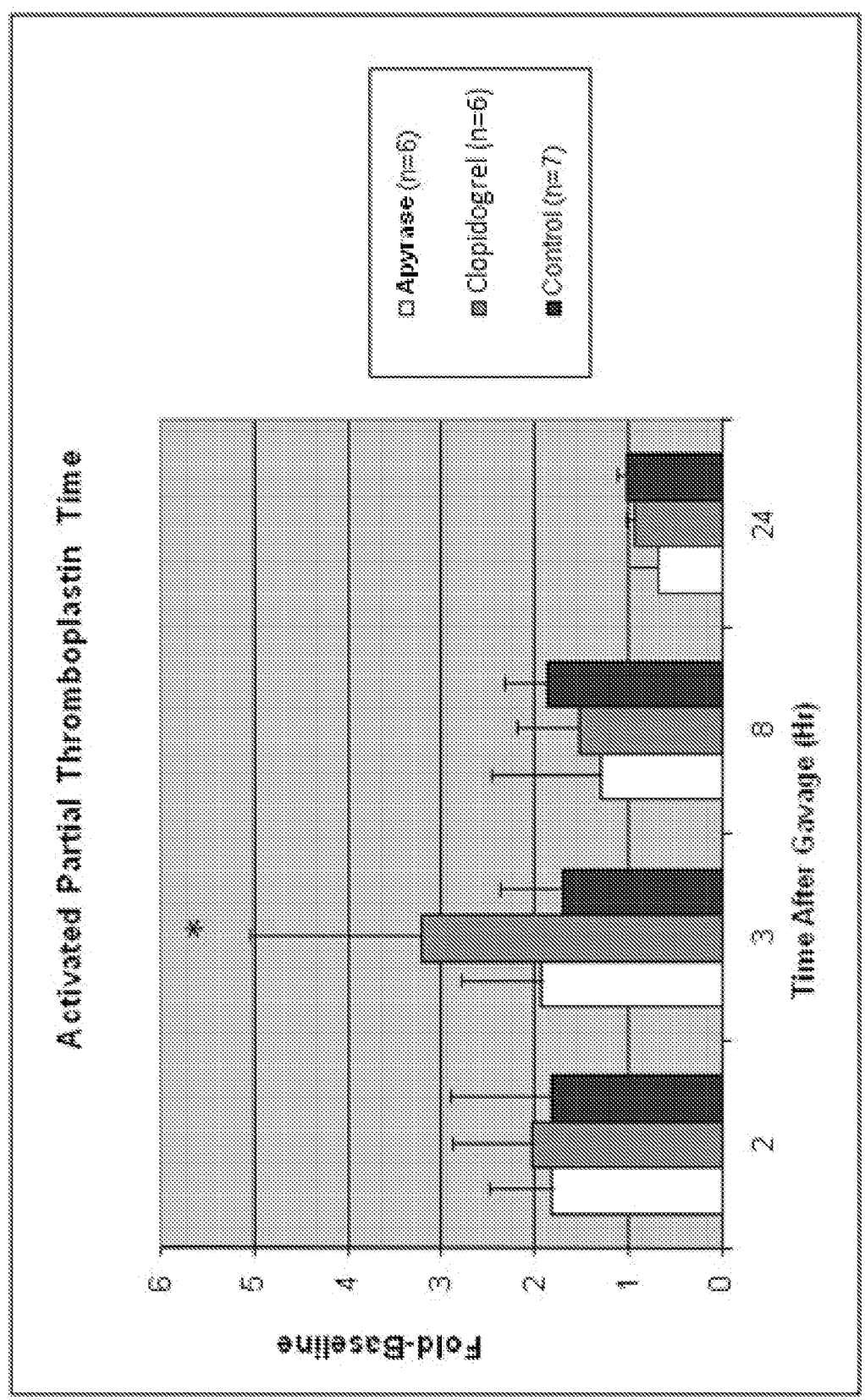
FIG. 6 shows activated partial thromboplastin times (aPTT) for various time points after lavage in pigs subject to coronary injury.

PT and aPTT were measured 2 h after gavage of aspirin or clopidogrel (the baseline before administration of apyrase agent), and 3, 8, and 24 h after gavage corresponding to 1, 6, and 22 h after administration of sol CD39L3 R67G T69R or the start of coronary injury and stenting. PT was increased significantly compared to baseline (p<0.001 by two-way ANOVA with repeated measures) in clopidogrel-treated pigs (FIG. 5). aPTT was increased modestly in all treatment groups during the time of heparinization, but the increase was significant only in clopidogrel-treated pigs (FIG. 6).

Template bleeding time is a standard assay for assessing bleeding risk during antithrombotic therapy that we have employed in previous studies in pigs. Bleeding time was measured 2 h after gavage of aspirin or clopidogrel (before administration of apyrase agent), and after 24 h with use of a scalpel cut applied to the edge of the ear. Clopidogrel-treated pigs showed marked elevations in bleeding times at both 2 and 24 h that were nearly 3-fold higher than the bleeding times in either apyrase agent or control pigs.

Blood loss from a surgical incision has been used more recently as an index of bleeding risk that might occur during major surgical procedures. Blood loss from a standardized incision of the abdominal wall was measured at the same intervals as for template bleeding times. Incisions were 4 cm long and approximately 1 cm deep through the skin and muscle layers (but avoiding incision of the peritoneum) on the mid- to lateral aspect of the abdominal wall. Blood was collected on pre-weighed gauze over 5 min. Clopidogrel treatment yielded a trend for an increase in blood loss by 24 h, but the differences compared with apyrase agent or control were not significant due to variability in the results.

Two markers of inflammation, C-reactive protein and tumor necrosis factor-alpha (TNF-alpha), were assayed in plasma samples collected serially beginning with a sample before angioplasty (2 h after gavage) to identify any possible benefits of apyrase agent on the post-angioplasty inflammatory process. C-reactive protein, which is produced by the liver in response to cytokine release, gradually increased in all treatment groups, but increased more markedly in the aspirin-treated controls by 24 h. Collection of samples over longer intervals may have shown greater differences between treatment groups for this marker. TNF-alpha levels were increased slightly at the time of angioplasty, possibly in response to surgery and anesthesia, and trended to decrease over time in all groups. The assay used was for human TNF-alpha, which was reported to crossreact with porcine TNF-alpha, but may have lacked sensitivity.

SUMMARY

These studies with apyrase agent in pigs undergoing coronary angioplasty and stenting show several important findings. First, a single IV bolus of apyrase agent inhibited acute platelet deposition on the stented coronary over the first 24 hours to an extent that was similar to pretreatment (2 h) with a single dose of clopidogrel, but greater than achieved by aspirin alone. Importantly, had the clopidogrel and apyrase agent been given at the same time before coronary injury, the benefit of clopidogrel would likely have been much less. Reduced platelet thrombus formation with apyrase agent or clopidogrel early after coronary injury may have contributed also to the preliminary observations of reduced neointimal hyperplasia within stented vessels after 30 days. However, the neointima appeared thinner in pigs given apyrase agent compared to those given clopidogrel. This provocative finding may reflect a benefit of apyrase agent on continuing platelet thrombus accumulation on the stented vessel or greater reduction in inflammation following treatment with apyrase agent. Although a marked reduction in inflammation could not be confirmed by plasma markers in these experiments, further analysis of the effects of apyrase agent on inflammation after coronary stenting appears warranted.

A second major finding was that pigs given apyrase agent did not have increased bleeding compared to those given clopidogrel. Template bleeding time, which is well accepted as an indication of relative bleeding risk was not affected by apyrase agent, but was markedly increased by clopidogrel. Blood loss from a deep skin and muscle incision analogous to a surgical-type wound was also not increased by apyrase agent, but trended to be increased at 24 h by clopidogrel.

Accordingly, these studies demonstrate that: 1) apyrase agent eliminates the bleeding risk observed with clopidogrel and may thereby increase safety in acute PCI patients; and 2) apyrase agent improves the efficacy of PCI compared with clopidogrel in terms of inhibition of post-procedure inflammation or other complications including development of neointimal hyperplasia.

Example 7

Apyrase Agent for Treating Bleeding Associated with tPA Use in Acute Myocardial Infarction in Dogs A well-established canine coronary thrombosis and fibrinolysis model was used to compare an apyrase agent to clopidogrel administered as adjunctive treatment with recombinant tissue plasminogen activator (rtPA).

Figure 7:
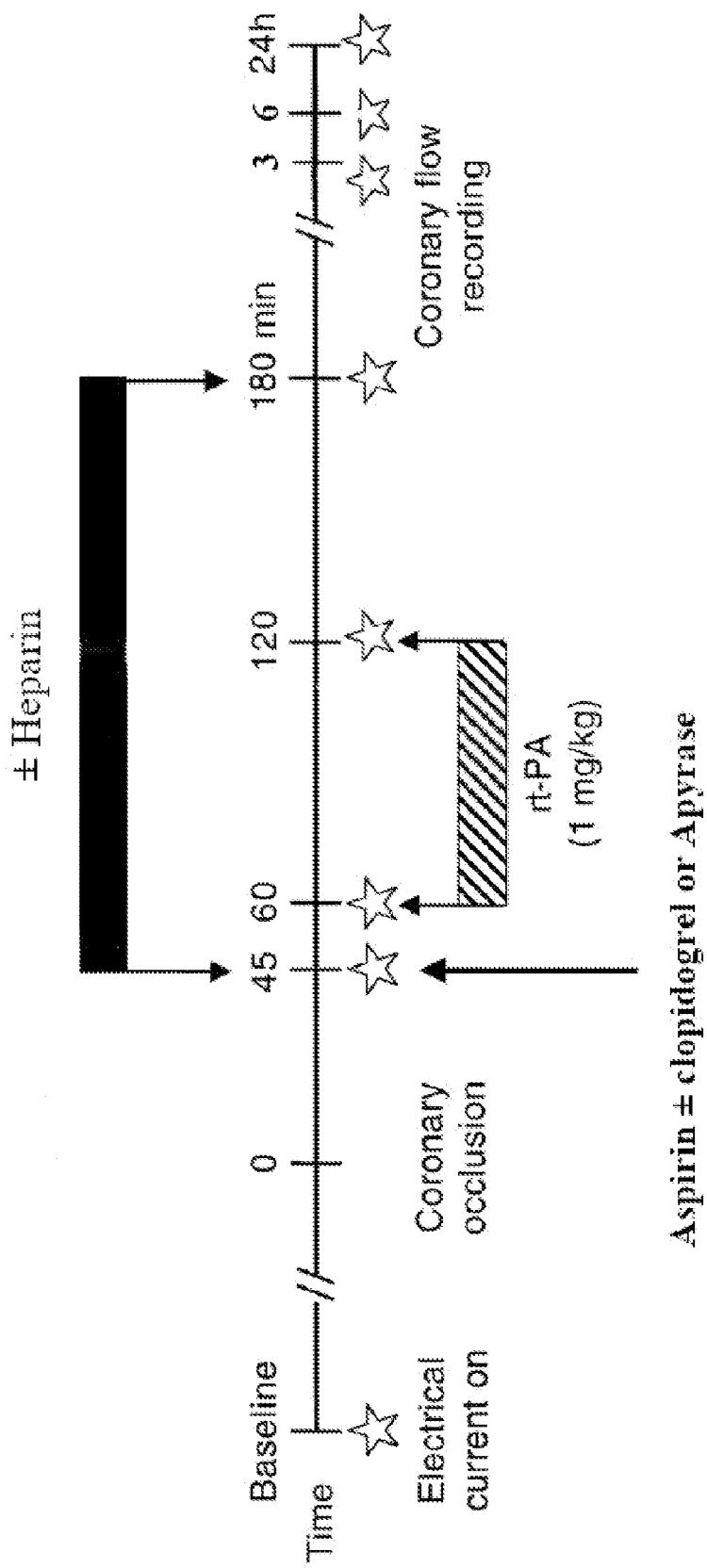
FIG. 7 shows an experimental protocol to test the effect of apyrase agent in dogs with myocardial infarction.

Thrombotic occlusion was induced by electrical injury to a coronary artery in dogs. Aspirin and clopidogrel were administered orally and apyrase agent was administered by intravenous injection 45 min after thrombotic occlusion. 100 U/kg of heparin was administered by intravenous injection 45 min after thrombotic occlusion followed by continuous infusion (50 U/kg/h) until 180 min after occlusion. Fibrinolysis was induced with rtPA 60 min after thrombotic occlusion and flow was monitored continuously for 24 h with an implanted Doppler flow probe. Buccal mucosa bleeding times, PT, and aPTT were measured as indices of bleeding risk. After 24 hours of reperfusion, infarct size was determined by Evan's blue and triphenyltetrazolium chloride double staining. This protocol is illustrated in FIG. 7.

Eighteen dogs were divided into three treatment groups (n=6 per group):
1) Clopidogrel (4 mg/kg, p.o.)
2) sol CD39L3 R67G T69R (0.25 mg/kg, IV)
3) sol CD39L3 R67G T69R (1 mg/kg, IV)

Baseline CBF was similar in the control and treatment groups. Reperfusion was achieved in all treatment groups within 51 min after r-tPA administration. Reocclusion occurred in all clopidogrel and low dose apyrase agent dogs within 230 min after fibrinolysis (Table 6). In contrast, the apyrase agent at 1 mg/kg completely prevented reocclusion in all the dogs tested. Compared to clopidogrel treatment, an apyrase agent decreases infarct area by 80% at low dose and 90% at high dose, either as a percent of left ventricular area or of ventricular area-at-risk.

TABLE 6

| Group | Reperfusion Time | Re-occlusion rate | Re-occlusion time |
| --- | --- | --- | --- |
| Aspirin (5 mg/kg) | 23' | 100% | 81' |
| Aspirin + clopidogrel (4 mg/kg) | 32' | 100% | 120' |
| Aspirin + apyrase at 0.25 mg/kg | 28' | 100% | 155' |
| Aspirin + apyrase at 1.0 mg/kg | 32' | 0 | |

After administration of tPA and heparin, prothrombin time (PT) and activated partial thromboplastin time (aPTT) values were increased in all animals. By the end of adjunctive therapy, there was an increased PT and aPTT in clopidogrel group, but not apyrase group. Bleeding time was significantly prolonged in clopidogrel group compared to the placebo group. In contrast, no detectable change in bleeding time was observed with apyrase agent treatment.

Conclusion

The adjunctive administration of an apyrase agent to r-tPA is more effective, faster and safer than clopidogrel in sustaining coronary artery recanalization, reducing infarct size and bleeding risk.

Example 8

Apyrase Protection of Cardiac Ischemic/Reperfusion Injury in Mice

A mouse model of cardiac ischemia/reperfusion injury was used to determine the effect of apyrase agent on infarct size. Myocardial ischemia was produced in C57BL/6J mice via left anterior coronary artery ligation. Mice were treated with apyrase agent (1 mg/kg, IV) or saline 5 min prior to 60 min of experimentally-induced myocardial ischemia or 50 min after ischemia (n=6-8 per group). After 24 hr of reperfusion, hearts were excised and area at risk and infarct size were determined by Evan's blue and triphenyltetrazolium staining.

Compared to the control group, apyrase agent treatment 5 minutes prior to the onset of ischemia resulted in approximately 50% reduction of infarct size. Representing the more common clinical situation in which a patient presents with signs of ischemia, apyrase agent was nearly equally effective when administered 50 min after ischemia as it was when administered prior to ischemia, again reducing infarct size by approximately 50%.

Example 9

Apyrase Agent for Treating Bleeding from Ischemia-Reperfusion Injury Associated with Transplantation Fischer 344 rats (Harlan Sprague Dawley, Inc, Indianapolis, Ind.), weighing 250 to 300 grams, were subjected to orthotopic left lung transplantation.

The cuff technique (Robson, S. C., et al., Semin. Thromb. Hemost. (2005) 31:217 was used. In brief, after general anesthesia with intraperitoneal pentobarbital (65 mg/kg), mechanical ventilation, systemic heparinization (300 units), and median laparosternotomy, donor rat lungs were flushed through the main pulmonary artery with 20 mL of cold (4° C.) low-potassium dextran glucose solution at 20 cm $H_2O$ pressure. In apyrase agent-treated groups, 0.1 mg/L apyrase agent was added to the cold preservation medium. The heart-lung block was then removed with the lungs inflated at end-tidal volume. The left lung graft was isolated, prepared, and stored in low-potassium dextran glucose at 4° C. until transplantation. After 18 hours of cold preservation, recipient animals were anesthetized, intubated with a 14-gauge catheter, and underwent a left thoracotomy. The pulmonary vessels and bronchus were anastomosed with a standard cuff technique. In the sham group, the rats underwent anesthesia and thoracotomy alone. In apyrase agent-treated groups recipients received treatment intravenously through the internal jugular vein 7 minutes after graft reperfusion. In dose response studies apyrase agent was administered at a dose of either 0.07, 0.22 or 0.66 mg/kg of recipient weight. In all other studies apyrase agent was administered at a dose of 0.66 mg/kg of recipient weight. In the vehicle-treated groups, rats received a saline bolus 7 minutes after reperfusion.

The function of the left lung was assessed 4 hours after transplantation. Rats in each group were reanesthetized with pentobarbital. After tracheostomy, the animals were mechanically ventilated with 100% oxygen and a laparosternotomy was performed. The right hilar structures were clamped to isolate the left lung graft. The animals were ventilated for 5 minutes at a tidal volume of 1.5 mL, a respiratory rate of 100 breaths/min, and 1.0 cm $H_2O$ of positive end-expiratory pressure. Arterial blood gas analysis was performed with blood samples obtained from the ascending aorta. The lungs were flushed with 20 mL of cold (4° C.) saline solution, and the lung graft was excised and divided into 3 separate sections. The upper and middle sections were snap frozen. The upper section was used for enzyme-linked immunosorbent assay (ELISA) and the middle section was used for myeloperoxidase (MPO) assay. The lower section was weighed, dried at 70° C. for 48 hours, and then reweighed for calculation of the wet/dry (W/D) ratio.

Quantitative MPO activity was determined also previously described (Krawisz, J. E., et al., *Gastroenterology* (1984) 87:1344). Optical density was measured at 460 nm with a spectrophotometer (model PMQ II; Carl Zeiss, Oberkochen, Germany). Color development was linear from 5 minutes to 20 minutes. One unit of enzyme activity was defined as 1.0 optical density unit per minute per milligram of tissue protein at room temperature.

Proinflammatory cytokine and chemokine measurement was made on lung samples which were homogenized with T-PER Extraction Reagent (Pierce, Rockford, Ill.). Lung homogenates were centrifuged twice at 10,000 rpm at 4° C. for 5 min, and the supernatants were collected. The content of tumor necrosis factor-α (TNF-α, interleukin-1β (IL-1β) and macrophage inflammatory protein-2 (MIP-2) were determined by using ELISA kits (BioSource International, Inc, Camarillo, Calif.) in accordance with manufacturer's instructions.

For TUNEL assay, lung specimens harvested 4 hours after reperfusion were perfused with 20 mL isotonic sodium chloride solution and inflation fixed with 20 mL HistoChoice (Amresco Inc, Solon, Ohio). Specimens were cut, mounted, de-paraffinized, and then steam-treated with Dako target retrieval solution (Dako, Carpentaria, Calif.) and quenched with 3% hydrogen peroxide. Assessment of lung cell apoptosis was performed with a TUNEL kit (Promega, Madison, Wis.) in accordance with manufacturer's instructions. For quantification of cell apoptosis, 15 randomly chosen fields were assessed for each group at a magnification of 400×.

For real-time PCR, total RNA was isolated by TRIzol® (Sigma, St. Louis, Mo.) from lung tissue in accordance with manufacturer's recommendations and reverse transcribed and amplified using QuantiTect SYBR® RT-PCR kit (Qiagen, Valencia, Calif.) and primer sets (Qiagen) specific for *Rattus norvegicus* Entpd2 (CD39) and the housekeeping gene Rn18s (18sRNA). RT-PCR was carried out on a Bio Rad ICycler™ at 30 min at 50° C., 15 min at 95° C. and then 40 cycles of 95° C. for 15 sec, 58° C. for 30 sec and 72° C. for 30 sec. Levels of intragraft CD39 were calculated by the AACT method using 18sRNA as a relative standard and represented through normalizing CD39 mean expression to CD39 mean expression in resting lung tissue.

For flow cytometry, lungs were digested in an RPMI 1640 solution containing Type 2 collagenase (0.5 mg/ml) (Worthington Biochemical Corporation, Lakewood, N.J.) and 5 U/ml DNAse (Sigma, St. Louis, Mo.) for 60 minutes. The digested lung tissue was then passed through a 70 μm cell strainer and treated with ACK lysing buffer. Cells were then stained with biotinylated anti-rat CD31 along with either goat-anti rat E-selectin (R&D Systems, Minneapolis, Minn.) or a goat immunoglobulin control IgG (eBioscience, San Diego, Calif.). Samples were then washed and stained with hamster anti-goat IgG PE (Invitrogen, Carlsbad Calif.) and anti-biotin APC-750 (eBioscience, San Diego, Calif.) and then analyzed for EC-specific E-selectin expression on a modified 5-color Becton Dickinson FACS SCAN using a $CD31^+$ expression gate.

For ATP/ADP assay, aliquots from 5.0 ml bronchoalveolar fluid samples were assayed for ATP and ADP using EnzyLight™ ATP and ADP assay kits (BioAssay Systems) in accordance with manufacturer's recommendations.

Evans blue dye (EBD) was used to determine lung microvascular permeability. EBD is a sensitive marker for pulmonary edema, and microvascular dysfunction was quantified by measuring the concentration of EBD within the lung. EBD solution (100 mg/ml) was prepared in phosphate-buffered saline (PBS; pH 7.4). A separate series of animals (n=5 each) underwent the same surgical procedure and received EBD solution (30 mg/kg) intravenously 5 minutes after reperfusion. Four hours after reperfusion, lung grafts were excised and snap frozen following flushing with 20 mL of PBS. To extract EBD, the lung tissue was homogenized in 5 mL of formamide. The homogenate was incubated at 37° C. for 24 hours and centrifuged at 3500 g for 30 minutes. The optical density of the supernatant was measured at 620 nm. The concentration of EBD was calculated from a standard curve of EBD-formamide solutions and expressed as milligrams of EBD per gram of wet lung weight.

A separate series of animals (n=5 each) underwent BAL cell counts at the time of sacrifice. The right hilum was clamped and the left lung was lavaged twice with saline (3.0 mL per lavage) through the tracheostomy. BAL fluid was centrifuged at 1500 rpm for 8 minutes. The pellet was resuspended in PBS, and total cell numbers were counted with hemocytometer using trypan blue solution (Mediatech, Herndon, Va.) to exclude dead cells. Neutrophil numbers were determined with a Hemavet® HV950FS (CDC Technologies, Oxford, Conn.).

Experimental means are represented with the standard error of the mean (SEM). Statistical analysis to assess significant differences between experimental groups was performed by using the Student's t test. Results were considered statistically different if $p<0.05$.

Results

Lung isografts underwent 18 hours of cold preservation prior to engraftment.

Apyrase agent improved graft histopathology and inhibited endothelial cell apoptosis. We inquired if apyrase agent treatment improved lung graft histopathology.

Using hematoxylin and eosin stain, apyrase agent-treated recipients showed less apparent alveolar hemorrhage and microvascular injury as compared to saline-treated recipients and only minimal changes in graft architecture when compared to sham lungs. These data suggested that the EC barrier is better preserved in apyrase agent-treated recipients. To examine this further we examined lung grafts for the presence of apoptotic EC by TUNEL stain. Consistent with previous observations in lung grafts subjected to prolonged cold ischemia there were many apoptotic EC in the lung graft alveoli of saline-treated recipients. In contrast, in the lung grafts of apyrase agent-treated recipients there were significantly fewer apoptotic EC indicating effective protection against vascular injury.

TUNEL positive EC nuclei were counted in randomly selected 400× fields and expressed as a mean±SEM with statistical significance **p<0.01 (N=7/group). Sham showed essentially no TUNEL positive EC X 400 times field while saline treated showed a mean number of 14. For apyrase treated, only an average of three TUNEL positive EC were found. Thus, instant apyrase agents are effective for preventing bleeding associated with transplantation and IRI.

Lung isografts were measured for intragraft CD39 mRNA 1 or 4 hours after transplantation using real-time PCR as described above.

Lung grafts from recipients following either 1 or 4 hours of reperfusion had significantly less intragraft CD39 transcripts relative to either lung tissue preserved for 18 hours prior to transplantation or lung tissue obtained from sham operated rats. These data suggested that there is a loss of ectoapyrase activity following lung transplantation.

Figure 8:
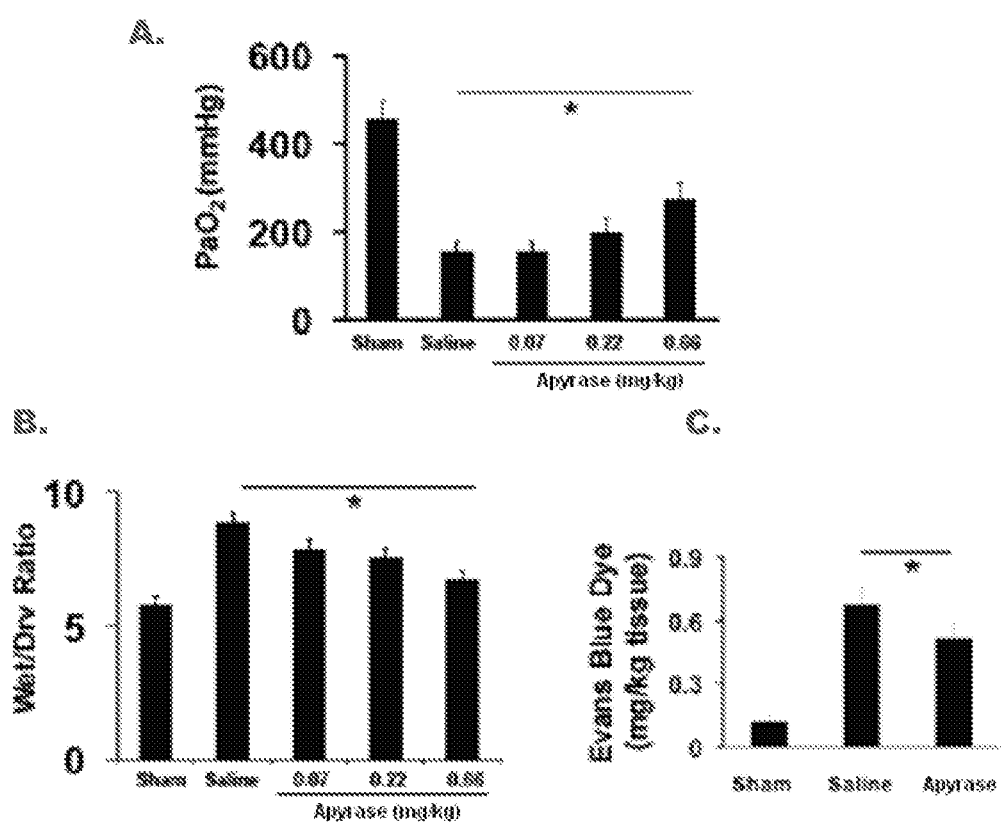
FIGS. 8A-8C depict lung function and vascular permeability following lung transplantation.

FIG. 8 shows the results of measures of lung function. Sham animals or lung graft recipients treated with saline or indicated amounts of apyrase agent four hrs post reperfusion were assessed for (FIG. 8A) arterial blood gasses at $FiO_2$ 1.0 expressed as a mean $PO_2$ (mmHg) or FIG. 8B mean wet to dry weight ratio. FIG. 8C shows mean percent exclusion of Evans blue dye in sham lungs or lung grafts treated with 0.66 mg/kg apyrase agent or saline 4 hours post reperfusion. These results are representative of at least 5 recipients per group and expressed as means±SEM with statistical significance as *p<0.05 or **p<0.01 between indicated groups Prior to 18 hours of cold preservation lung grafts were either flushed with apyrase agent (0.1 mg/mL) or vehicle (saline) and then graded amounts of apyrase agent or a bolus of saline was administered intravenously 7 minutes following reperfusion. Compared to saline-treated recipients, apyrase agent-treated recipients showed a trend towards better lung function at a dose of 0.22 mg/kg and significant improvement at a dose of 0.66 mg/kg. In accordance with improved lung function pulmonary edema trended to lower mean levels at a 0.22 mg/kg dose of apyrase agent and was significantly attenuated at a 0.66 mg/kg dose of apyrase agent.

The apyrase agent-mediated effects on lung graft IRI associated with apyrase agent-specific activity was assessed by measuring the concentration of extracellular purinergic nucleotides. BAL fluid was obtained from saline-treated or apyrase agent-treated recipients and measured for ATP and ADP levels by bioluminescence assay 4 hours after engraftment. Relative to saline-treated lung graft recipients, apyrase agent-treated lung graft recipients had significantly lower concentrations of both ATP and ADP in the BAL fluid indicating that augmenting apyrase agent-specific activity helps preserve lung graft function. Results are representative of at least 4 recipients per group and are expressed as means±SEM with statistical significance as **p<0.01 between indicated groups.

Apyrase agent treatment also inhibits the sequestration of neutrophils in lung grafts. Lung graft IRI is exacerbated by the rapid accumulation of neutrophils in the airways and lung interstitium. We therefore asked if apyrase agent-mediated improvement of lung graft function was associated with the regulation of inflammatory cell trafficking into lung grafts. Lung isografts were cold preserved for 18 hours before engraftment and total cell accumulation along with neutrophil numbers in the BAL was assessed 4 hours after transplantation. Apyrase agent-treated lung graft recipients had significantly fewer cells in the BAL. Additionally, we observed a significant decrease in the numbers of neutrophils recovered from the airways of apyrase agent-treated lung graft recipients as compared to saline-treated lung graft recipients. MPO activity, a relative measure of neutrophil graft tissue infiltration, was also reduced in lung grafts of apyrase agent-treated recipients along with the expression of E-selectin, a critical marker of endothelial cell activation that promotes neutrophil adhesion and sequestration.

Apyrase agent treatment attenuates intragraft proinflammatory cytokine and chemokine synthesis. The reduction in neutrophil accumulation in lung grafts of apyrase agent-treated recipients suggested attenuation of intragraft inflammatory gene expression. In particular the inflammatory cytokines TNF-α and IL-1β promote endothelial cell activation while the chemokine MIP-2 drives neutrophil chemotaxis into graft tissue. We investigated if apyrase agent treatment regulated the intragraft expression of these inflammatory mediators following 18 hours of cold ischemia and 4 hours engraftment. Apyrase agent significantly attenuated the intragraft levels of TNF-α, IL-1β and MIP-2 protein suggesting that augmentation of apyrase activity down-regulates gene expression associated with tissue inflammation.

Figure 9:
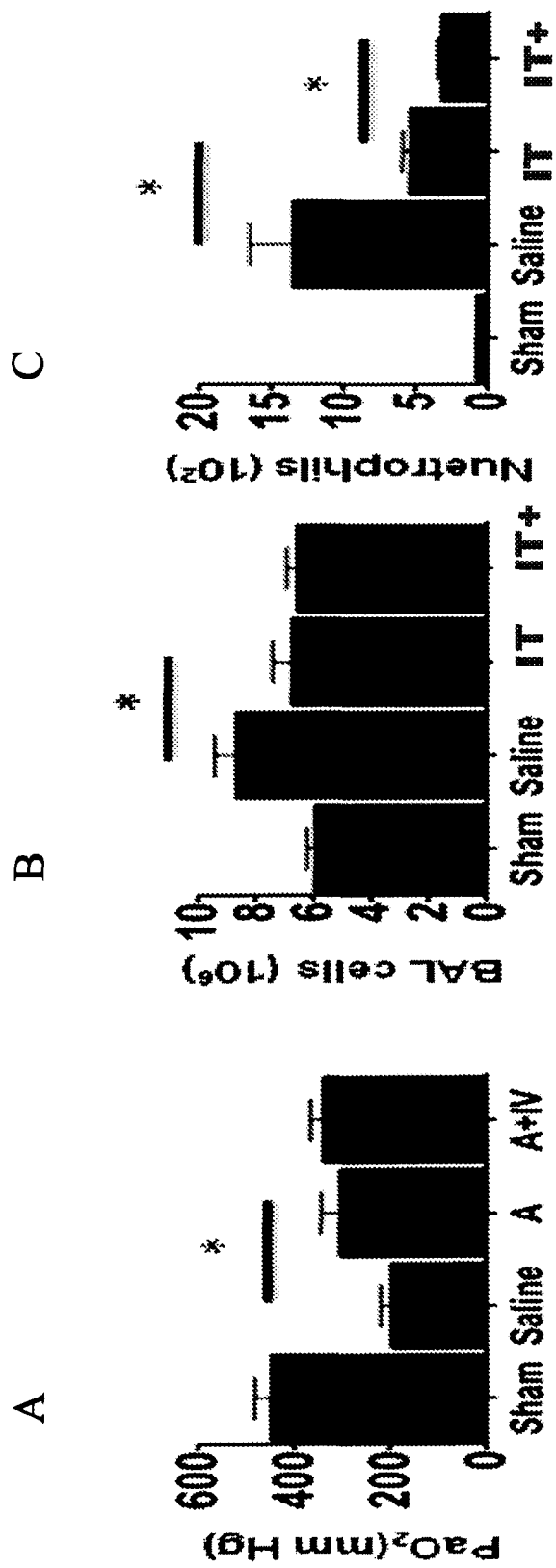
FIGS. 9A-9C show apyrase agent treatment inhibits inflammatory cytokines and chemokine production.

Lung grafts following 4 hrs of reperfusion or sham lungs were homogenized for total protein and assessed for intragraft TNF-α, IL-1β, and MIP-2 levels by ELISA. Results are representative of at least 5 animals per group and expressed as mean±SEM with a statistical significance as *p<0.05 and **p<0.01, and are shown in FIG. 9.

The level of TNFa was reduced from about 75 pg/mg in the saline treated group to about 35 pg/mg in the apyrase treated group. The level of IL-1β was reduced from about 2,200 pg/mg in the saline treated group to about 1,100 pg/mg in the apyrase treated group. MIP-2 was reduced from about 1,800 pg/mg in the saline treated group to about 1,300 pg/mg in the apyrase treated group. In all cases, the sham levels were lower than either the saline treated or apyrase treated groups.

It is demonstrated here that treatment with apyrase agent can reduce bleeding (e.g., lung graft alveolar hemorrhage and pulmonary edema) and attenuate lung graft IRI. Apyrase agent administration just following reperfusion is effective at improving $PaO_2$, inhibiting pulmonary edema as well as attenuating other markers of physiological lung injury when compared to saline-treated lung transplant recipients.

Example 10

Airway Administration of Apyrase Agent for Ischemia Reperfusion Injury and Function Following Lung Graft F344 rat lung grafts were flushed and cold preserved in Apyrase agent solution (0.2 mg/L) and engrafted into syngeneic F344 recipients.

At 5 minutes post-reperfusion 1 ml apyrase agent solution (1 mg/kg) (N=6) or an equivalent volume of saline carrier was administered to the trachea at approximately 5 minutes post-reperfusion (N=7). In additional group of lung graft recipients that were treated with apyrase agent intratracheally, apyrase agent was also administered intravenously at 7 minutes post-reperfusion at 0.66 mg/kg (N=9). Lung graft oxygenation, airway cellularity and airway granulocyte numbers were measured 4 hours post-reperfusion. We noted no gross pulmonary hematomas in any treatment groups.

$PaO_2$ (mm Hg) was improved from 200 in saline treated animals from about 200 in saline treated animals to about 300 or 320 in those treated intratracheally (IT) or by IT and IV. Airway administration of apyrase agent was significantly effective at improving lung function as measured by lung graft mediated oxygenation. As shown in FIGS. 9A and 9B, apyrase agent significantly prevented the accumulation of inflammatory cells in the airway. Most notable was the over 50% reduction of neutrophils in the airway indicating the effectiveness of apyrase agent at preventing airway inflammation in lung grafts injured by prolonged cold preservation.

When apyrase agent airway treatment was combined with additional IV bolus of apyrase agent in lung graft oxygenation or total cellularity in the airways was not significantly changed. However, in this treatment group, a significant reduction in neutrophil accumulation in lung graft airways when compared to apyrase agent airway treatment alone was observed, as compared to $12 \times 10^2$ neutrophils for saline control, $5 \times 10^2$ for airway alone and $3 \times 10^2$ for airway and IV.

The airway administration of apyrase agent was comparatively effective at preventing lung injury as compared to single dose IV administration of apyrase agent. The airway administration route has the distinct advantage of localizing the effect of apyrase activity to the lung graft and thus may prevent any possible systemic effects of apyrase agent such as systemic immunosuppression or bleeding.

Example 11

Treating Bleeding from Allogenic Transplantation Rejection

Figure 10:
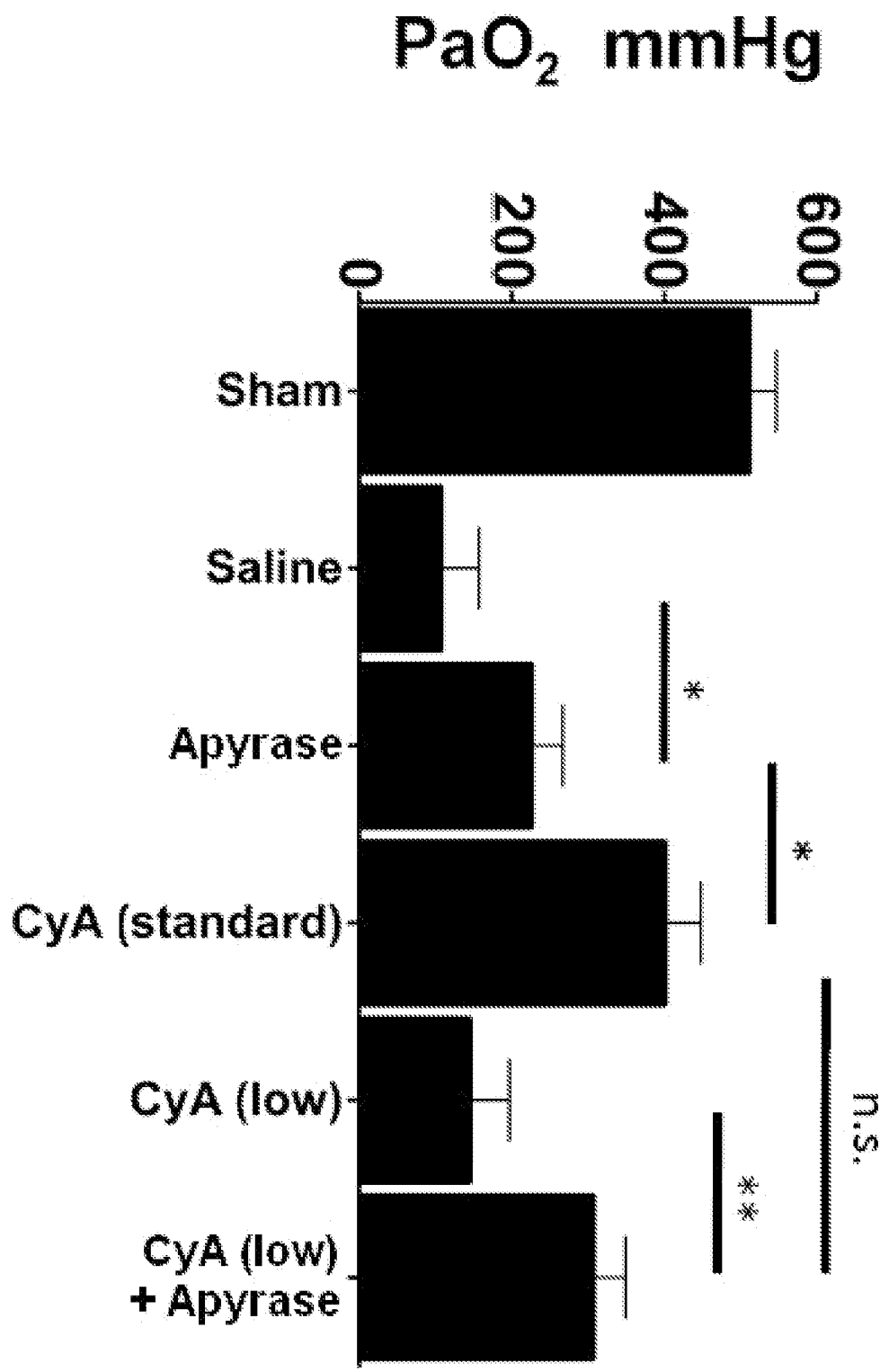
FIG. 10 shows the effect of apyrase agent (alone or in combination with cyclosporine) on lung function.
Figure 11:
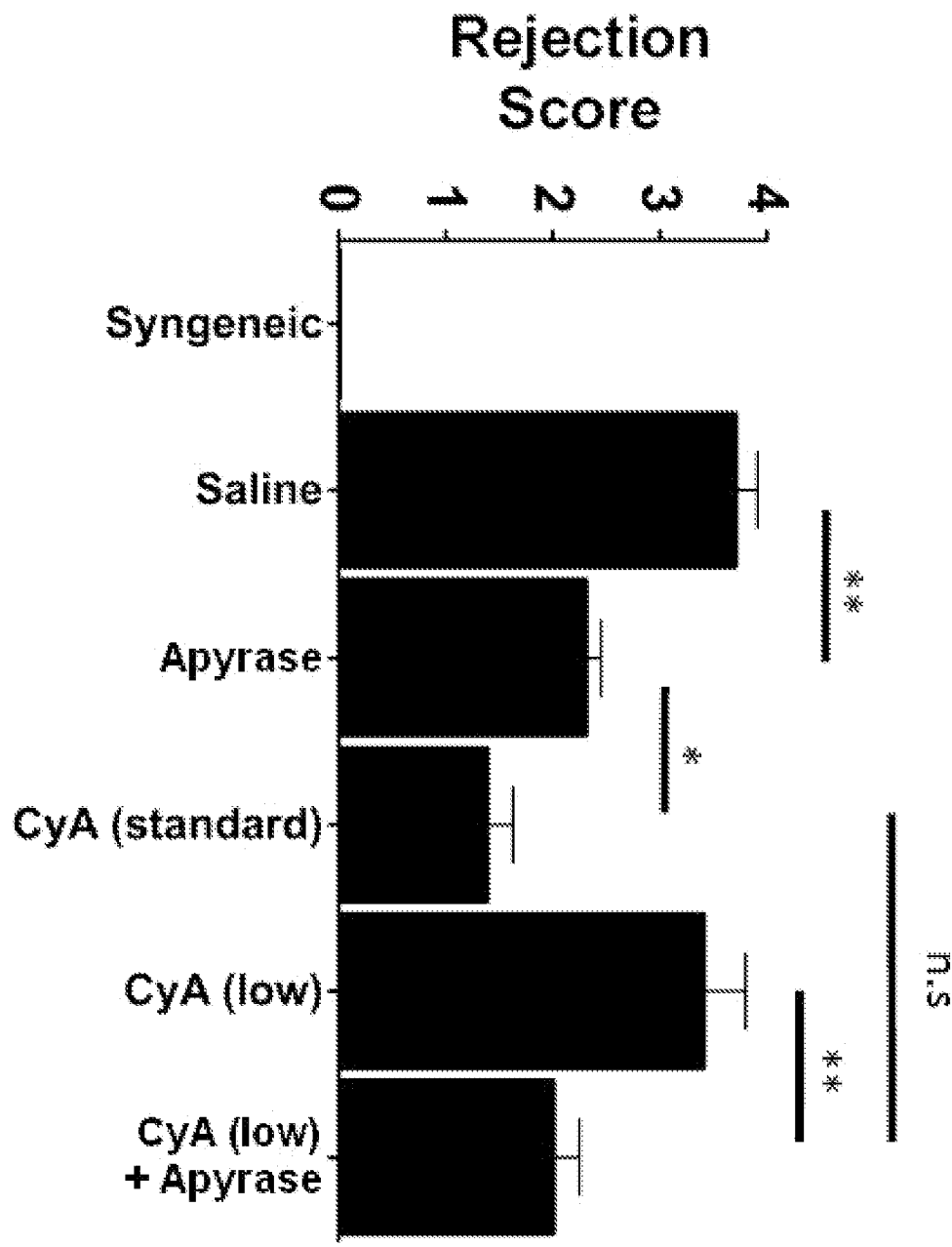
FIG. 11 shows the effect of apyrase agent (alone or in combination with cyclosporine) on rejection of allogenic lung transplantation.

The efficacy of apyrase agent in attenuating alloimmune responses was demonstrated using a rat lung transplant model. Lewis donor lungs stored for a minimal cold ischemia time of 1 hr were engrafted into allogenic Wistar Furth recipients and treated for 7 days in the following manner:

1. Saline: Received Saline 250 μl/day
2. Apyrase: Received Apyrase agent, 0.66 mg/kg/day IV
3. CyA (standard): Received Cyclosporine A 25 mg/kg/day, IP (standard dose used in previous studies)
4. CyA (low): Received Cyclosporine A 5.0 mg/kg/day, IP (sub optimal dose)
5. CyA (low)+apyrase agent: Received Cyclosporine A 5.0 mg/kg/day, IP and Received apyrase agent, 0.66 mg/kg/day IV On post-operative day 7 recipients were evaluated for lung graft function by assessing $PaO_2$ (FIG. 10) and then sacrificed and scored blindly for vascular rejection (FIG. 11) using the ISHLT scoring system by a pathologist who routinely evaluates lung allograft rejection. The ISHLT scoring criteria is a scale from where a score of A0 there is no evidence of vascular rejection as in completely syngeneic recipients (e.g., Lewis to Lewis lung transplantation) to A4 as is almost always observed in Lewis to Wistar Furth Recipients. Statistical differences between treatment groups (n=10) were determined by the student t test where significance differences were assessed as $p<0.05$. Control group for the alloimmune response was the Lewis to Lewis lung transplant combination.

As shown, these data indicate that apyrase agent is effective at suppressing alloimmune responses in lung allograft recipients. Combination of cyclosporine with apyrase permits lowering the cyclosporine dose.

Example 12

Apyrase Agent for Treating Bleeding Associated with Hemorrhagic Stroke

Objective: This study will examine whether EN-apyrase, can reduce hematoma growth in a model in which intracerebral hemorrhage is induced by intracerebral injection of collagenase in rats; and whether EN-apyrase can reduce edema formation after intracerebral infusion of 100 μL of blood in the rat.

Methods: In a collagenase model of intracerebral hemorrhage, young or aged Fisher 344 rats are administered 2 μL injection of saline containing collagenase (type VII) (Rosenberg, G. A., et al., *Stroke* (1990) 21:801-807). In an autologous blood model, rats are administered an intracandate injection of 100 μL autologous whole blood. EN-apyrase or vehicle is injected intravenously at different time points. Hemorrhage area is measured for each section of brains and total hematoma volume is calculated by summing the clot area in each section and multiplying by the distance between sections. Hemoglobin in brain supernatant is measured spectrophotometrically. Brain water and ion content is calculated by weighting wet and dehydrated brain slices. Neurological deficits are assessed using forelimb placing and corner turn tests.

Results: Systemic administration of EN-apyrase, when begun within 12 hours after intracerebral hemorrhage, will significantly reduce hematoma growth by 30%. The treatment also will reduce brain edema, attenuate ventricle enlargement, candate atrophy, and neurological deficits.

The invention claimed is:

1. A method to decrease bleeding or the risk of bleeding in a subject which method comprises
   (a) identifying a subject diagnosed as in need of said decrease or at such risk and
   (b) administering to said subject an effective amount of an apyrase agent,
   wherein said subject has suffered or is expected to suffer vascular injury that disrupts the blood vessels of said subject.

2. The method of claim 1 wherein said vascular injury is caused by pathophysiological conditions, ultrasound, surgery, clot removal, administration of anticoagulants, administration of thrombolytics, administration of antiplatelet agents, reperfusion treatments or transplantation or combination thereof.

3. The method of claim 1 wherein said subject has suffered a stroke and is administered tissue plasminogen activator (tPA) or who has suffered hemorrhagic stroke caused by hypertension, trauma or other pathophysiological conditions.

4. The method of claim 1 which further comprises administering one or more additional pharmaceutical agent.

5. The method of claim 1 wherein the apyrase agent is a soluble CD39L3 apyrase agent.

6. The method of claim 5 wherein said apyrase agent is soluble CD39L3 R67G T69R.

7. The method of claim 1 wherein said apyrase agent is administered parenterally or by inhalation.

8. A method to preserve the function of a transplanted organ, which method comprises treating the organ to be transplanted or treating a transplant recipient receiving said organ and identified as diagnosed as in need of inhibition of bleeding with an effective amount of an apyrase agent.

9. The method of claim 8 wherein the organ is lung.

10. The method of claim 9 wherein the apyrase agent is a soluble CD39L3 apyrase agent.

11. The method of claim 10 wherein said apyrase agent is soluble CD39L3 R67G T69R.

12. The method of claim 8 wherein said apyrase agent is administered parenterally or by inhalation.

* * * * *